US010441689B2

United States Patent
Weisman et al.

(10) Patent No.: US 10,441,689 B2
(45) Date of Patent: Oct. 15, 2019

(54) METHODS AND DEVICES FOR THREE-DIMENSIONAL PRINTING OR ADDITIVE MANUFACTURING OF BIOACTIVE MEDICAL DEVICES

(71) Applicant: Louisiana Tech Research Corporation, Ruston, LA (US)

(72) Inventors: Jeffery Adam Weisman, Buffalo Grove, IL (US); Connor Nicholson, Monroe, LA (US); David Mills, Monroe, LA (US)

(73) Assignee: Louisiana Tech Research Corporation, Ruston, LA (US)

( * ) Notice: Subject to any disclaimer, the term of this patent is extended or adjusted under 35 U.S.C. 154(b) by 684 days.

(21) Appl. No.: 14/822,275

(22) Filed: Aug. 10, 2015

(65) Prior Publication Data

US 2016/0038655 A1 Feb. 11, 2016

Related U.S. Application Data

(60) Provisional application No. 62/035,492, filed on Aug. 10, 2014, provisional application No. 62/042,795, (Continued)

(51) Int. Cl.
| | |
|---|---|
| *A61L 31/16* | (2006.01) |
| *B33Y 30/00* | (2015.01) |
| *B33Y 70/00* | (2015.01) |
| *A61L 27/14* | (2006.01) |
| *A61L 27/54* | (2006.01) |

(Continued)

(52) U.S. Cl.
CPC ............ *A61L 31/16* (2013.01); *A61L 15/22* (2013.01); *A61L 15/44* (2013.01); *A61L 27/14* (2013.01); *A61L 27/54* (2013.01); *A61L 29/04* (2013.01); *A61L 29/16* (2013.01); *A61L 31/04* (2013.01); *B29C 64/106* (2017.08); *B29C 64/112* (2017.08); *B29C 64/20* (2017.08); *B33Y 30/00* (2014.12); *B33Y 70/00* (2014.12);
(Continued)

(58) Field of Classification Search
CPC ... A61F 2240/001; B33Y 10/00; B33Y 30/00; B33Y 70/00; B33Y 80/00
See application file for complete search history.

(56) References Cited

U.S. PATENT DOCUMENTS

| | | | |
|---|---|---|---|
| 5,518,680 | A | 5/1996 | Cima |
| 9,192,912 | B1 | 11/2015 | Mills et al. |

(Continued)

FOREIGN PATENT DOCUMENTS

| | | |
|---|---|---|
| WO | 2013013038 A2 | 1/2013 |
| WO | 2014075185 A1 | 5/2014 |

OTHER PUBLICATIONS

PCT Application No. US2015/044467; International Search Report for Applicant Louisiana Tech University Foundation; a division of Louisiana Tech University Foundation, Inc. dated Jan. 7, 2016.

*Primary Examiner* — Stella K Yi
(74) *Attorney, Agent, or Firm* — Jones Walker LLP

(57) ABSTRACT

A method for manufacturing a bioactive implant including the steps of (a) forming a mixture of an bioactive agent and a setting agent capable of transitioning from a flowable state to a rigid state; (b) converting the mixture into a flowable state; and (c) transitioning the mixture into a solid state in a shape of the implant.

19 Claims, 16 Drawing Sheets

Related U.S. Application Data filed on Aug. 27, 2014, provisional application No. 62/117,949, filed on Feb. 18, 2015.

(51) Int. Cl.

| | | |
|---|---|---|
| *A61L 29/04* | (2006.01) | |
| *A61L 29/16* | (2006.01) | |
| *A61L 31/04* | (2006.01) | |
| *A61L 15/22* | (2006.01) | |
| *A61L 15/44* | (2006.01) | |
| *B29C 64/106* | (2017.01) | |
| *B29C 64/112* | (2017.01) | |
| *B29C 64/20* | (2017.01) | |
| *B33Y 10/00* | (2015.01) | |
| *B29L 31/00* | (2006.01) | |

(52) U.S. Cl.
CPC . *A61F 2240/001* (2013.01); *B29L 2031/7532* (2013.01); *B33Y 10/00* (2014.12)

(56) References Cited

U.S. PATENT DOCUMENTS

| | | | |
|---|---|---|---|
| 2006/0188546 A1 | 8/2006 | Giroux | |
| 2007/0225544 A1* | 9/2007 | Vance | A61M 37/0069 600/8 |
| 2009/0157087 A1* | 6/2009 | Wei | A61B 17/7097 606/99 |
| 2010/0203100 A1* | 8/2010 | Cobian | A61L 27/34 424/423 |
| 2013/0338423 A1* | 12/2013 | Nakaji | A61N 5/1027 600/8 |
| 2014/0116749 A1 | 5/2014 | Shoemaker et al. | |
| 2014/0163664 A1 | 6/2014 | Goldsmith | |
| 2015/0290280 A1* | 10/2015 | Petrak | A61L 15/46 604/151 |

\* cited by examiner

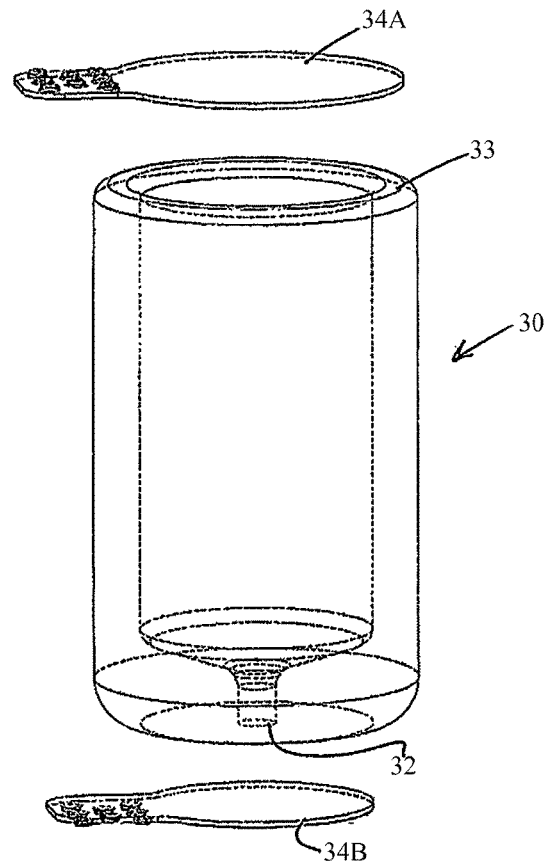
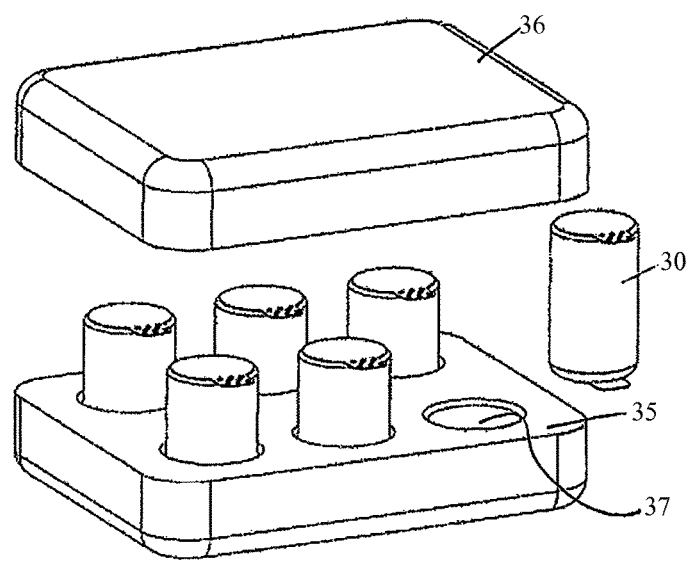
FIGURE 18
FIGURE 19

METHODS AND DEVICES FOR THREE-DIMENSIONAL PRINTING OR ADDITIVE MANUFACTURING OF BIOACTIVE MEDICAL DEVICES

CROSS-REFERENCE TO RELATED APPLICATIONS

This application claims the benefit under 35 USC 119(e) of US Provisional Application Nos. 62/035,492 filed Aug. 10, 2014; 62/042,795 filed Aug. 27, 2014; and 62/117,949 filed Feb. 18, 2015; all of which are incorporated by reference herein in their entirety.

BACKGROUND OF THE INVENTION

There are several types of 3D fabrication. These include but are not limited to fused deposition modeling that is normally seen in the personal consumer market using PLA or ABS plastic filament. In this method layer by layer plastic deposition is used to build a construct. In personal consumer versions 1.75 mm or 3 mm plastic filaments are run through a printing mechanism that heats and deposit the plastic in thin layers. Cheap consumer versions already allow for fine resolutions ranging from 50 um to 400 um. There are additional 3D fabrication methods such as selective laser sintering that fuse metal powders at a much finer resolution in layers, and injection molding which entails the injection of molten fabrication material into a mold, then rapid cooling of the material to create the desired device. Many of these methods are described in detail in "A Review of Additive Manufacturing," by Wong and Hernandez in ISRN Mechanical Engineering 2012 Article ID 208760. More specific examples of injection molding can be found in "A review of micro-powder injection moulding as a microfabrication technique" and "Recent Methods for Optimization of Plastic Injection Molding Process—A Retrospective and Literature Review" found in Journal of Micromechanics and Microengineering Article ID 043001 and International Journal of Engineering and Science and Technology Volume 2, 2010, respectively. Also incorporated by reference is the article Weisman, Jeffery A., et al. "antibiotic and chemotherapeutic enhanced three-dimensional printer filaments and constructs for biomedical applications." International Journal of Nanomedicine 10 (2015): 357 as well as the doctoral dissertation of Jeffery Adam Weisman Nanotechnology and additive manufacturing platforms for clinical medicine: An Investigation Of 3D Printing Bioactive Constructs And Halloysite Nanotubes For Drug Delivery And Biomaterials by Weisman, Jeffery A., Ph.D. Louisiana Tech University. 2014: 287 pages; 3662483.

3D printing by fused deposition modeling requires a plastic filament. A commercial extrusion device can normally make this filament. Normally plastic pellets of the desired material are run through the extrusion machine to create a filament. These pellets are normally the same or similar to those used in injection molding. The high costs of filament combined with the low cost of injection molding pellets has led to the recent creation of personal filament extrusion devices. The Lyman filament extruder was one of the first general personal designs to be built by the ends user or DIY for a low cost. This then lead to the sale of cheaper consumer oriented extrusion devices. One of the first personal filament extruders is Extrusionbot, LLC out of Phoenix Ariz. Custom 3D print filaments have been created with unique properties for circuit design as seen in "A Simple, Low-Cost Conductive Composite Material for 3D Printing of Electronic Sensors" by Simon Leigh 2012 DOI: 10.1371/journal.pone.0049365.

The general operation of filament extrusion devices is relatively simple. Pellets are poured into a hopper. They pass into a chamber or pipe with a moving auger in side. The pellets are moved down the pipe by auger. The chamber is heated by a heating mechanism to cause the pellets to melt and a melt-flow to occur. The heat level can be customized to the desired temperature. The end of the chamber or pipe will have a die with a hole drilled in with the diameter of the desired filament. As the molten plastic exits the die it will rapidly harden creating a filament. For certain materials, extra cooling measures must be taken, however this is not often seen with PLA or ABS (common 3D printing materials).

Most consumer filament extruders and printers use PLA or ABS plastic. Although there are more novel filaments that are for sale made from pellets such as nylon or a saw dust/plastic mix called laywood. This allows for fabrication of very unique filaments for unique constructs. To color PLA or ABS plastic pellets, a coloring powder is added into the hopper of the extruder. This colorant is normally not uniformly distributed but this is not usually visible to the naked eye.

Plastic melting point or meltflow temperatures are an intrinsic property of the material, and can be provided by the manufacturer. To enable ease of extrusion of the material, the heat applied to the extruding material must approach this point, but not exceed as a full melt of the plastic is not desired. Should a full melt be achieved, the material will not cool rapidly enough upon exit from the device to achieve a uniform diameter desired by the user. It has long been known that there are many variables in determining melt flow temperatures and material handling as seen in "Polymer Melt Flow Instabilities in Extrusion: Investigation of the Mechanism and Material and Geometric Variables" by Ballenger Trans. Soc. Rheol. 15, 195 (1971) and "The Case for Polylactic Acid as a Commodity Packaging Plastic" by Sinclair DOI:10.1080/10601329608010880.

Filament extruders need to be cleaned before differing batches of filament are extruded. This cleaning process can be difficult as plastics and additives can adhere to both the pipe and auger. Purging the extruder between batches takes substantial amounts of time. In medical situations requiring different plastics this could cause time delays between unique extrusions. Additionally, the need for sterilization would require the entire extrusion machine to be disassembled.

In the context of sterilization, it should be noted that an extruder for filaments is normally run from 160-220 Celsius depending on the plastic used, and that a 3D printer head normally runs from 200-230 Celsius depending upon the material and the surrounding environmental conditions. These temperatures are highly variable depending on the material used and the environmental conditions in which the materials are being printed. For example, Polycaprolactone (PCL) plastics melt at 60 Celsius and have been printed at 160 Celsius, however this still is not normally significant sterilization for many medical applications. This can be seen in the published application "Use of polycaprolactone plasticizers in poly(vinyl chloride) compounds," US 20140116749 A1.

There have been multiple instances in the medical profession of quick fabrication of proto-type medical devices in practical and emergency situations. Practical applications where this is seen include the use of rapidly curing mixtures of poly-methyl methacrylate powder and liquid methylmethacrylate (a known cytotoxic material and carcinogenic) for use in implantation of devices such as antibiotic loaded beads or as cushioning material for hip replacements. A plastic trachea for an infant was recently printed to be used as an emergency airway until a more stable implant could be devised. "Treatment of severe porcine tracheomalacia with a 3-dimensionally printed, bioresorbable, external airway splint" David A. Zopf; Colleen L. Flanagan; Matthew Wheeler; Scott J. Hollister; Glenn E. Green JAMA Otolaryngology—Head and Neck Surgery. 2014; 140(1):66-71.

Implanting standard plastics can be dangerous since bacteria easily adhere to them. This is problem in both medical and food processing. It can be seen in PVC endotracheal tubes as shown in Biomaterials. 2004 May; 25(11):2139-51 "Inhibition of bacterial adhesion on PVC endotracheal tubes by RF-oxygen glow discharge, sodium hydroxide and silver nitrate treatments." This can also be seen in Maple Syrup digest October 1985 "Bacterial Adhesion to plastic tubing walls" by Warren King. The current level of medical printing technology would benefit from the ability to affordably add bioactive elements to devices or use non-toxic plastics to overcome potential implantation infections or inherent implant toxicity that may occur.

One issue with plastics that do not degrade such as PMMA involves the need for the later surgical removal of antibiotic beads when delivering antibiotics. Additional information on PMMA biomaterials can be found within US patents application and the references they incorporate, numbered but not limited to: application Ser. No. 13/446,775 Filed: Apr. 13, 2012 Title: Ceramic Nanotube Composites with Sustained Drug Release Capability for Implants, Bone Repair and Regeneration.

The literature shows a clear need for better designed medical related 3D printing methods and materials. In particular, methods and equipment to create bioactive or drug eluting constructs.

Summary of Selected Embodiments of the Invention

One embodiment of the present invention is a method for manufacturing a bioactive implant. The method includes the steps of (a) forming a mixture of an bioactive agent and a setting agent capable of transitioning from a flowable state to a rigid state; (b) converting the mixture into a flowable state; and (c) transitioning the mixture into a solid state in a shape of the implant.

Another embodiment of the present invention is a 3D printer cartridge. The cartridge includes a frame and a plunger mounted on and movable relative to the frame; a drive assembly is mounted on the frame and configured to move the plunger relative to the frame; a nozzle assembly is mounted on the frame where the nozzle assembly includes a nozzle aperture; and a heating element is configured to heat at least a portion of the nozzle assembly.

A further embodiment is an extruder device including (a) frame having a barrel portion and a handle configured to be gripped by a human hand; (b) a plunger mounted in and movable within the barrel portion; (c) a drive assembly mounted on the frame and configured to move the plunger relative to the frame; (d) a nozzle assembly mounted on one end of the barrel portion, the nozzle assembly including a nozzle aperture; and (e) a heating element configured to heat at least a portion of the nozzle assembly.

BRIEF DESCRIPTION OF THE DRAWINGS

FIG. 18 illustrates one embodiment of a capsule used in the disclosed extruder devices.

FIG. 19 illustrates a case for storing the capsules shown in FIG. 18.

DETAILED DESCRIPTION OF SELECTED EMBODIMENTS

Figure 1:
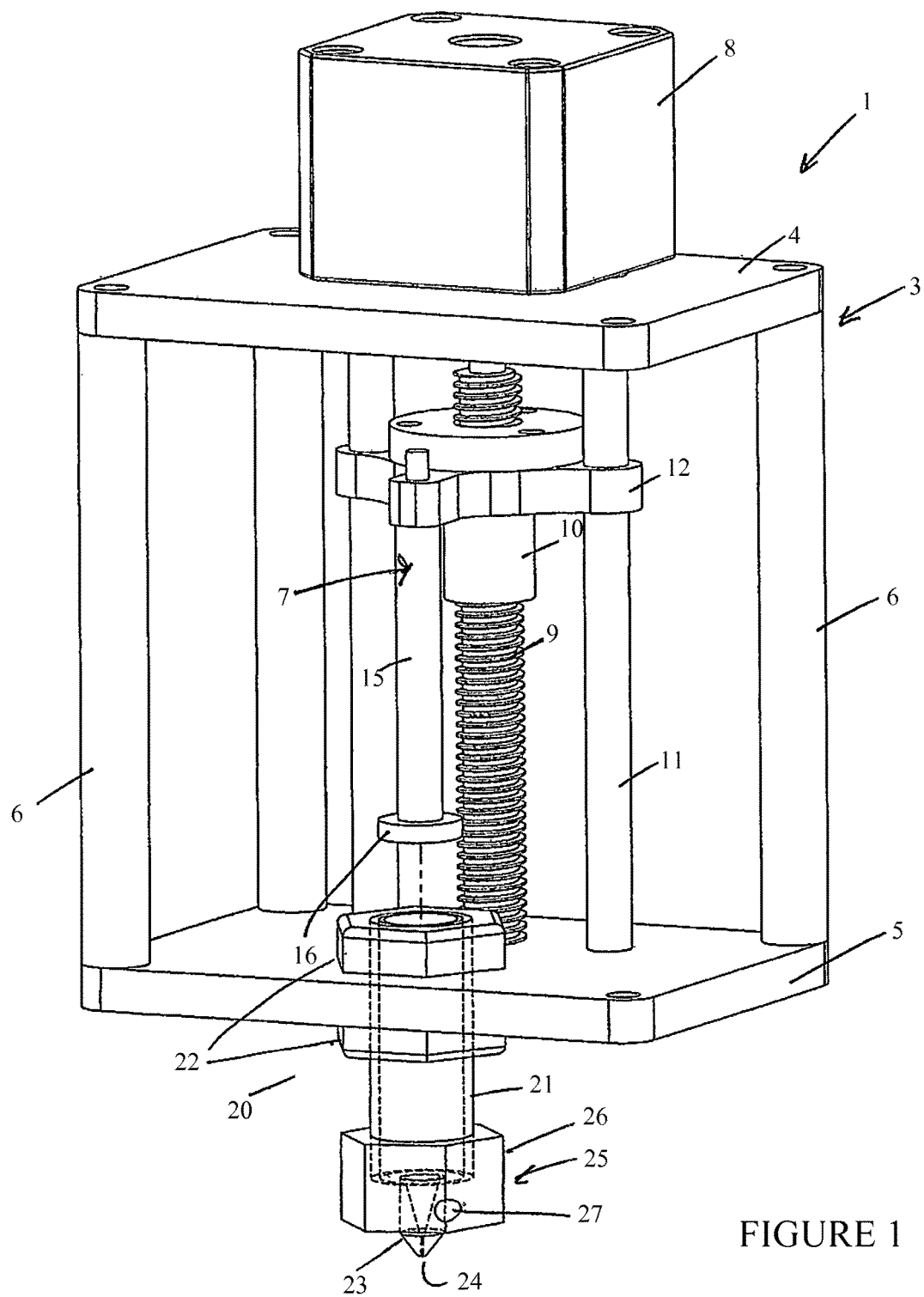
FIG. 1 illustrates one embodiment of a 3D printer cartridge.

As suggested above, one embodiment of the invention is a method of manufacturing a bioactive implant including the steps of forming a mixture of an bioactive agent and a setting agent capable of transitioning from a flowable state to a rigid state. The mixture is converted into a flowable state and then the mixture is transitioned into a solid state in a shape of the implant. As used herein, the term "implant" includes not only conventional medical implants (e.g., replacement joints, stints, catheters, screws, rods, meshes, intrauterine devices, etc.), but also any type of construct which may have medical application in or on a human or other animal body (e.g., sutures, dressings, medicated beads or filaments for insertion in or application to the body, etc.). The setting agent is defined in more detail below, but can be any material which transitions between a flowable state and a rigid state, typically dependent on a melt flow temperature. Nonlimiting examples are polymers typically used in 3D printing techniques and certain conventional bone cements. The "bioactive agent" (also sometimes referred to as an "additive" herein) is also defined in more detail below, but can be virtually any substance having a biologically therapeutic effect. Nonlimiting examples include antimicrobials, antiseptics, chemo-therapeutics, hormones, and vitamins. In many embodiments, the setting agent and bioactive agent are mixed and then placed in an extrusion device which heats the mixture to a flowable state before or as the mixture is extruded in a particular form, e.g., as by a conventional 3D printer.

FIGS. 1 to 4 illustrate one embodiment of a fused deposition modeling ("FDM") style print head (or "printer cartridge") for creating bioactive implants. As suggested generally in FIG. 1, this 3D printer cartridge 1 includes a frame 3, a plunger 15, a drive assembly 7 mounted on the frame 3, and a nozzle assembly 20. This embodiment of frame 3 is formed by the upper plate 4 and lower plate 5, spaced apart by the spacer columns 6. The nozzle assembly 20 extends through lower plate 5 and includes the tubular nozzle body 21 retained in place by positioning hex-nuts 22. The nozzle tip 23 is formed on the end of body 21 and includes the terminal nozzle aperture 24. The heating element 25 is also positioned on body 21. In the illustrated embodiment, heating element 25 is hex-nut threaded onto body 21 and has an aperture 27 for insertion of a heat generating device such as resistive heating element or thermistor (not shown in FIG. 1). The stated heating methods maintain temperature via pulse modulation or other standard regulating method.

Figure 2:
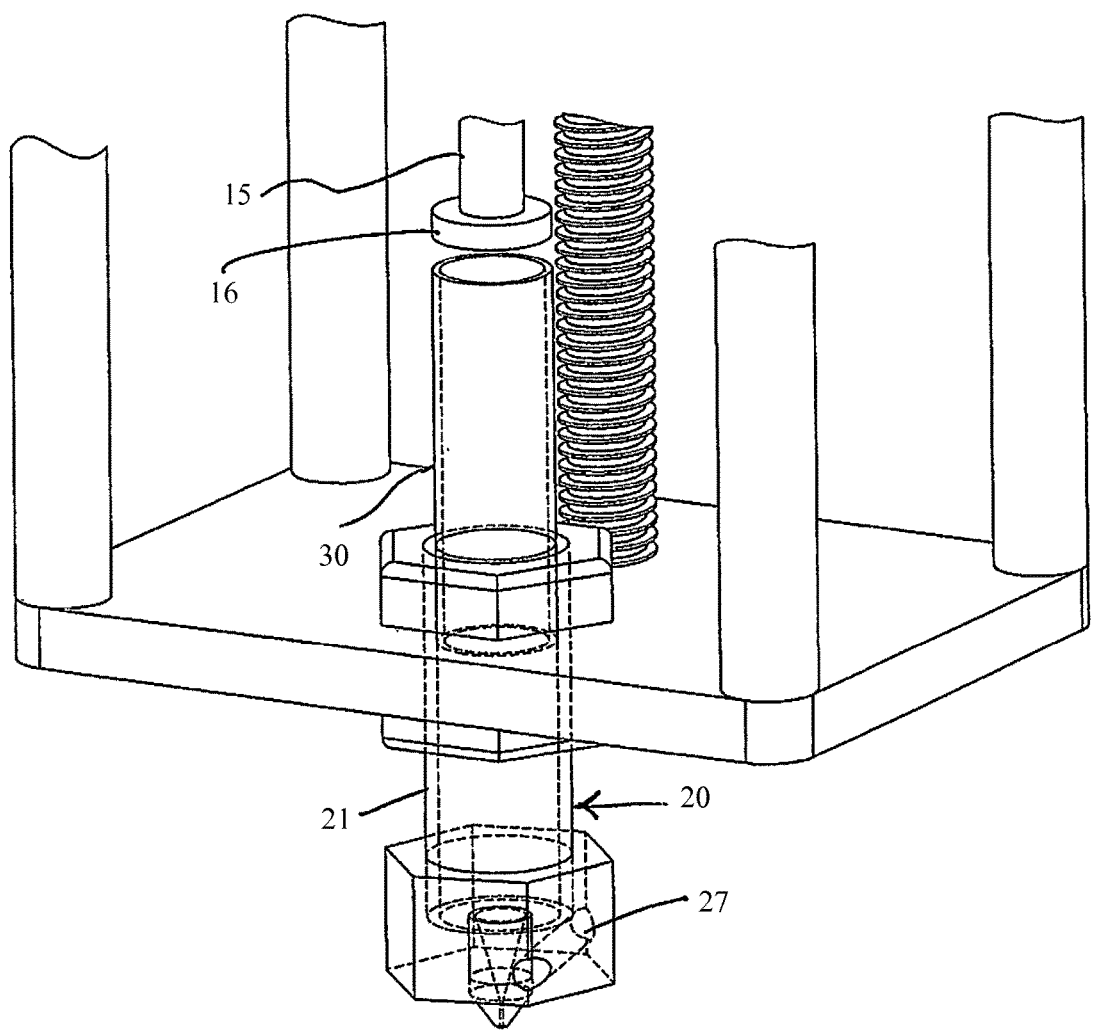
FIG. 2 illustrates a detailed view of the FIG. 1 nozzle assembly.

The plunger 15 having a plunger head 16 is positioned to travel into nozzle body 21. As used herein, "plunger" means any type of plunger, piston, bulb, rod, or other moving member operating to transmit force or pressure. The position of plunger 15 relative to nozzle body 21 is controlled by the drive assembly 7. Drive assembly 7 generally includes motor 8, threaded drive rod 9, and drive collar 10 having internal threads engaging the external threads of drive rod 9. Drive collar 10 includes collar guide 12 which has two apertures slidingly engaging guide rods 11 extending between the upper and lower plates 4,5. Plunger 15 is in turn fixed to a portion of collar guide 12. Since collar guide 12 holds drive collar 10 against rotation, it may be readily understood how motor 8, by rotating drive rod 9, will cause drive collar 10 to move up and down along drive rod 9. Thus, the control of motor 8 may be used to control the position of plunger 15. FIG. 2 suggests how a capsule 30 fits within nozzle body 21. In this embodiment, capsule 30 is a cylindrical tube and will contain the substance to be extruded out of nozzle assembly 20, e.g., a polymer stock material mixed with a bioactive agent as described above. The outer diameter of head 16 of plunger 15 will be slightly smaller than the inner diameter of capsule 30. The capsule may be a metal, ceramic, glass or thermo-resistant plastic container that can withstand the pressure and heating involved in the printing process. One method is envisioned wherein the plunger fits in the capsule like an caulk gun extrusion assembly. Alternatively, it would be possible to have a flexible capsule that compresses the contents in an accordion-like manner. In the latter case the piston would not have to fit within the capsule. It can be envisioned how the lowering of plunger head 16 into capsule 30 will force the polymer/bioactive agent through the nozzle aperture 24 as the polymer is raised to its meltflow temperature by heating element 25. It will be understood that this configuration of printer cartridge 1 exposes the nozzle assembly and plunger to the polymer/bioactive agent at each use. To 3D print a different polymer/bioactive agent, a new, sterile plunger 15 and nozzle assembly 20 would be positioned within the printer cartridge in order to avoid cross-contamination issues.

Figure 3A:
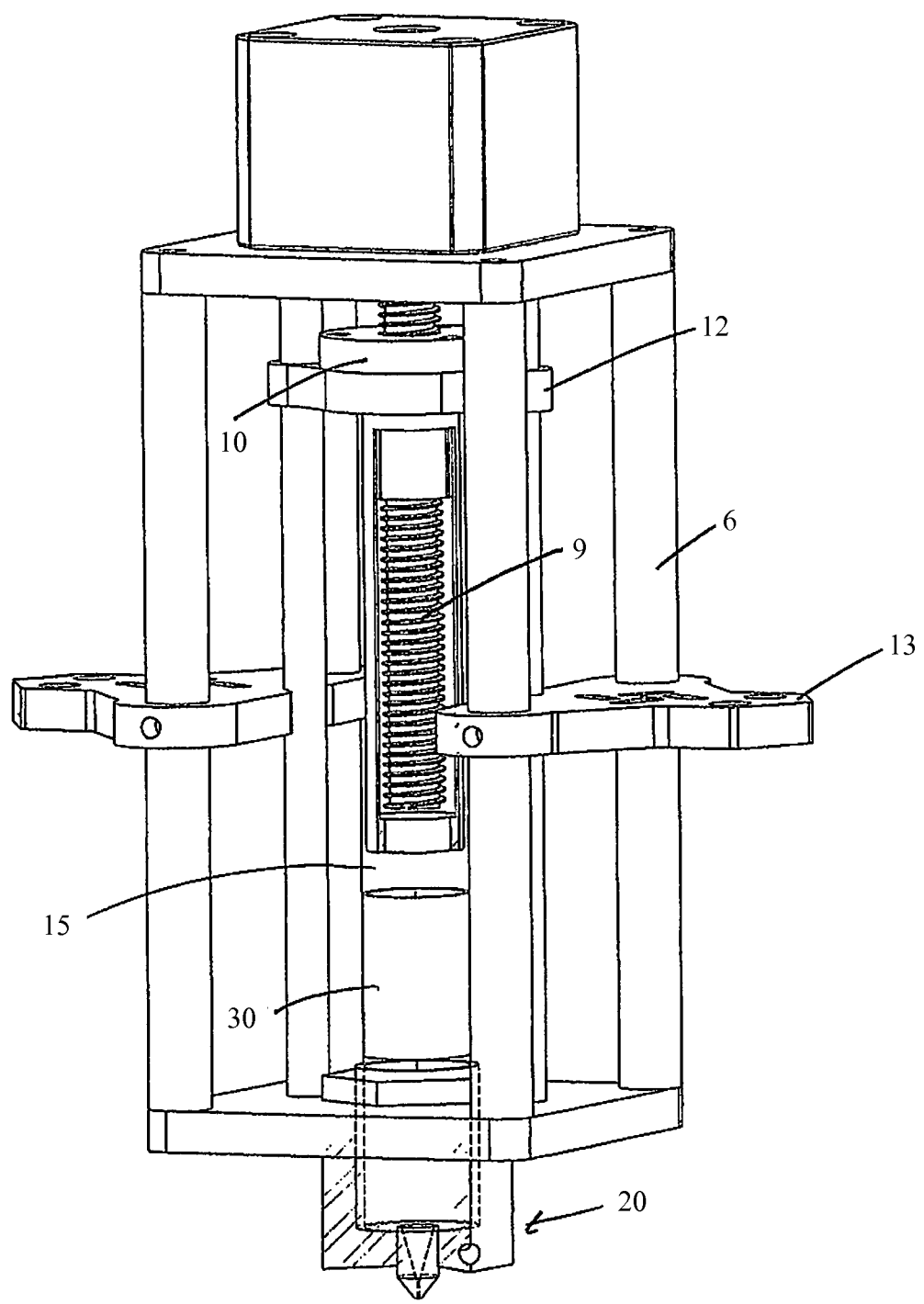
FIG. 3A illustrates a second embodiment of a 3D printer cartridge.
Figure 3B:
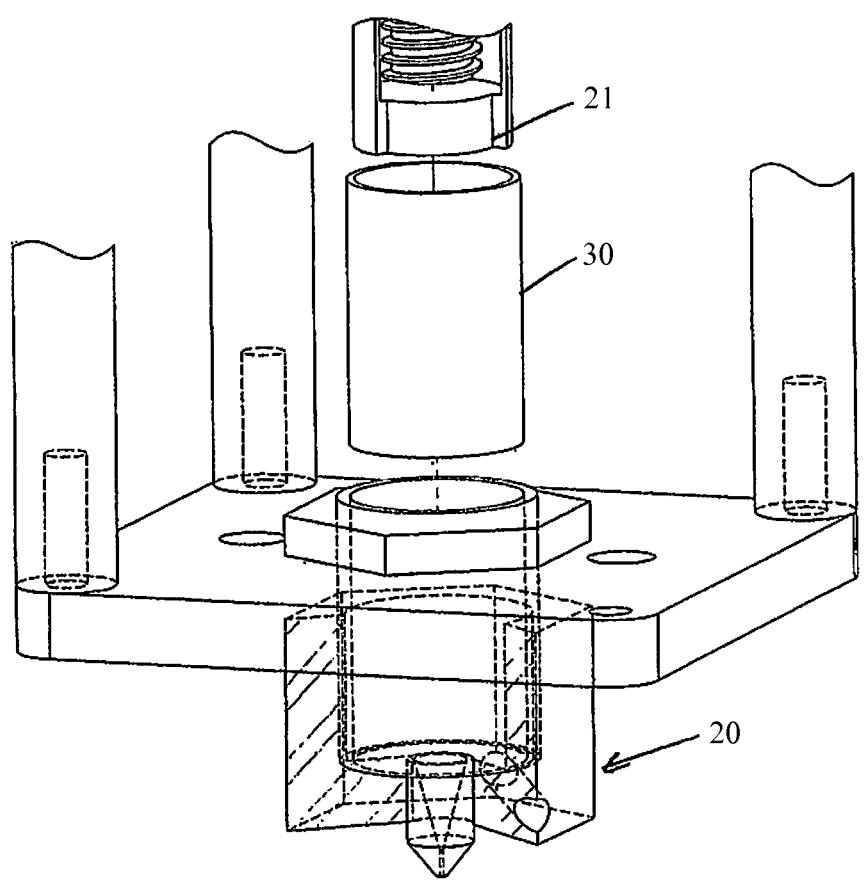
FIG. 3B illustrates a detailed view of the FIG. 3 nozzle assembly.
Figure 4:
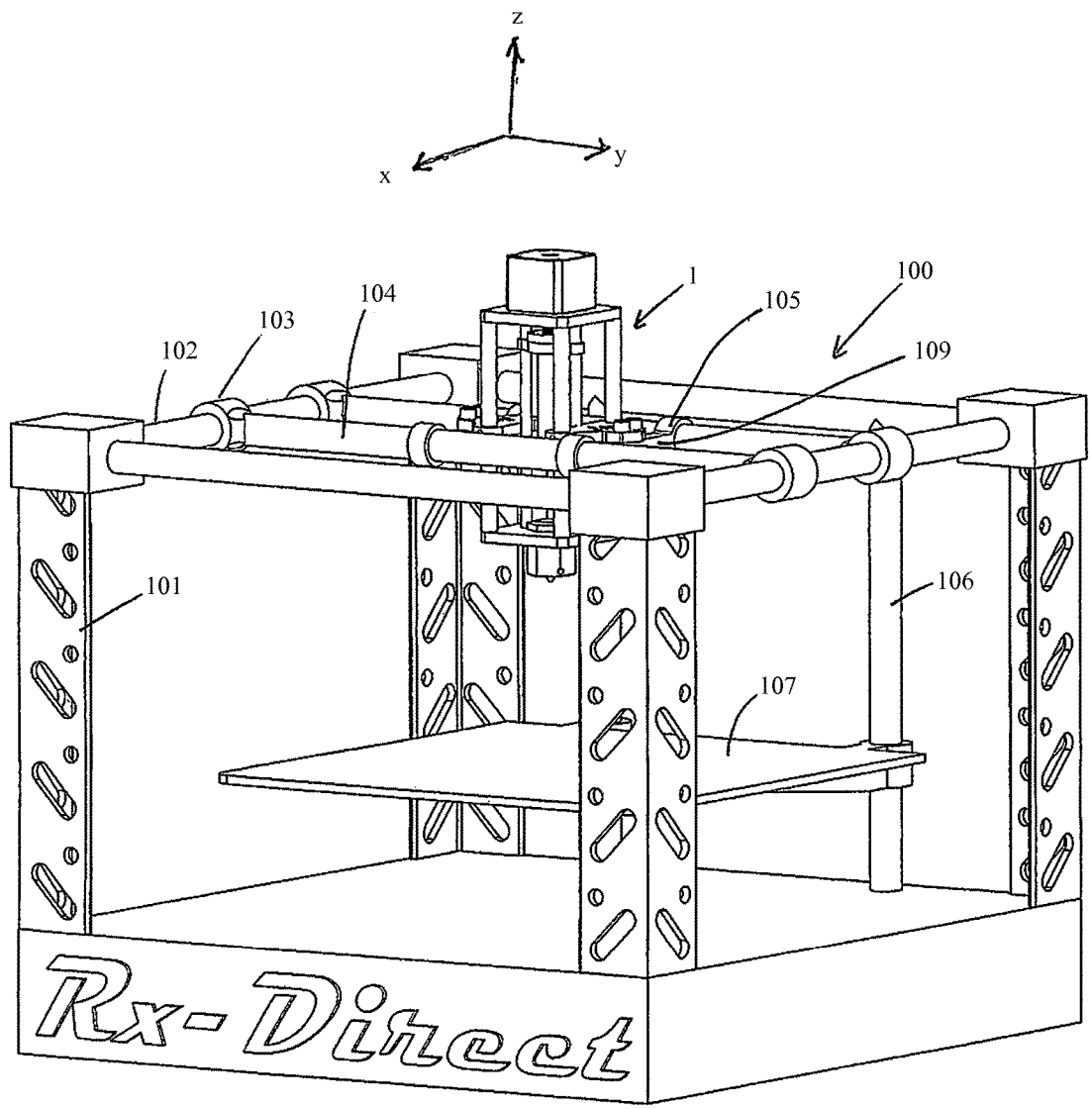
FIG. 4 illustrates the printer cartridge positioned in a 3D printer.
Figure 5:
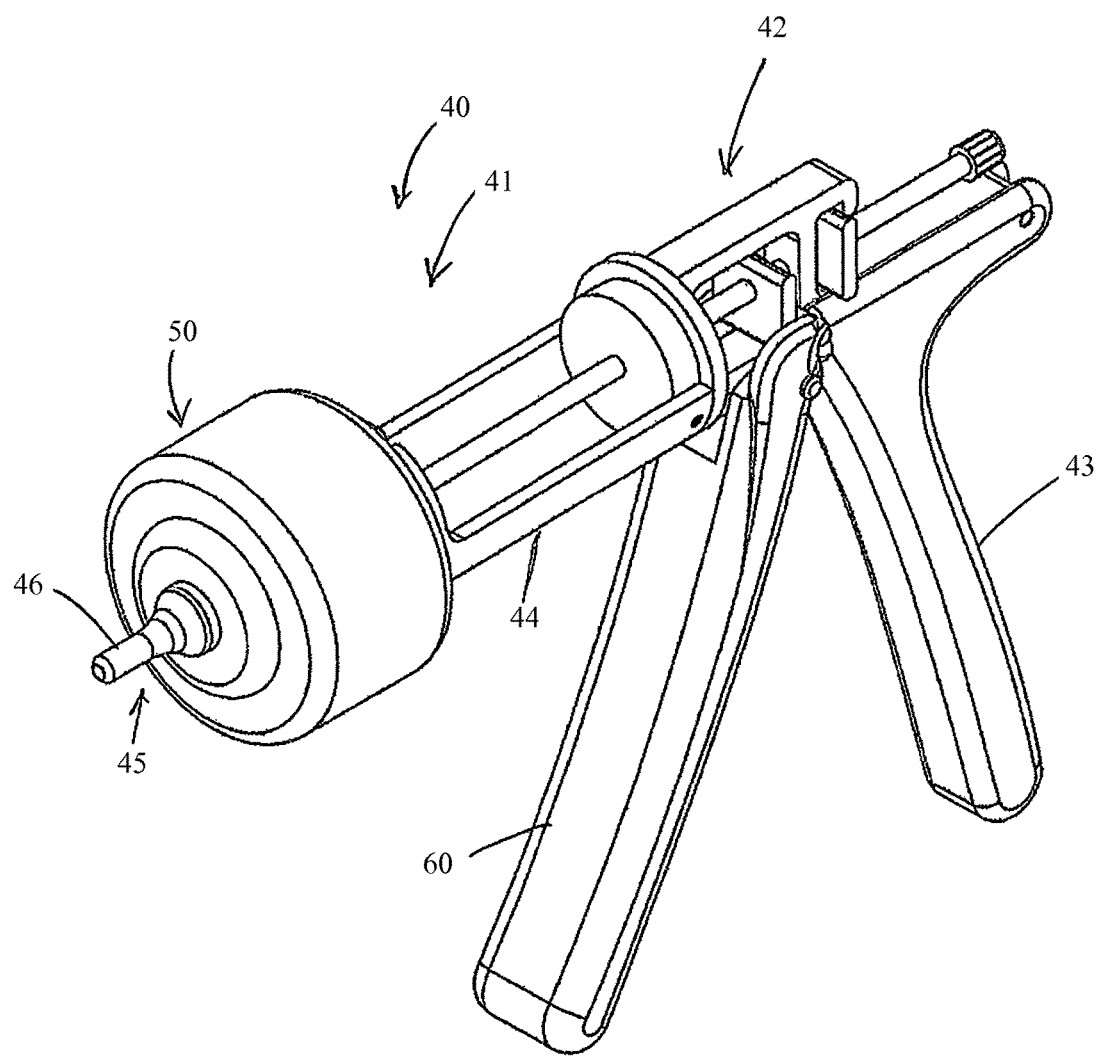
FIG. 5 illustrates a perspective view of one embodiment of an extruder device.
Figure 6:
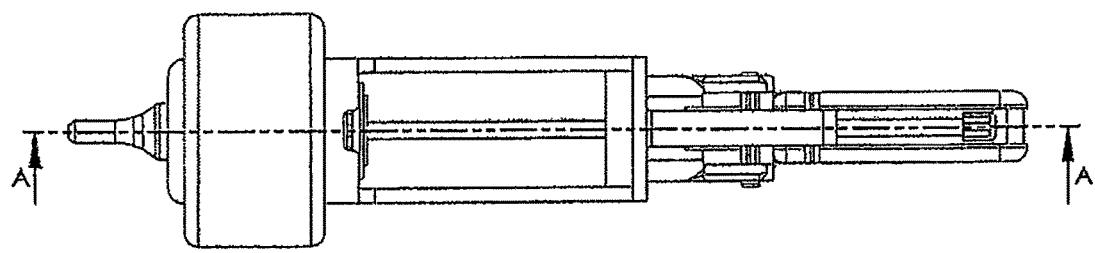
FIG. 6 illustrates a top view of the FIG. 5 extruder device.

FIGS. 3A and 3B illustrate a slightly modified embodiment of the printer cartridge 1. In this embodiment, the plunger 15 is a hollow cylinder that is attached to and extends below drive collar 10. Threaded drive rod 9 extends into the hollow portion of plunger 15 and nozzle assembly 20 is positioned directly below drive rod 9. Additionally, FIG. 3 shows attachment plates 13 connected to frame spacer columns 6. Attachment plates 13 will function to position the printer cartridge in the 3D printer device. FIG. 4 conceptually illustrates a 3D printer 100 with a printer cartridge 1 positioned thereon. 3D printer 100 is composed of printer frame members 101 which bears the x-axis support rods 102 on which the x-axis collars 103 travel. Although not explicitly shown, it will be understood that x-axis support rods 102 (and the y, z, axis support rods described below) could be threaded members. Rotation of the threaded x-axis support rods (by motors not shown) would cause travel of the x-axis collars, and thus positioning of printer cartridge 1 in the x-direction. Similarly, movement in the y-direction is accomplished by the y-axis collars 105 moving on y-axis support rods 104. FIG. 4 suggests how cross-beams 109 are attached to the y-axis collars and cross-beams 109 form the connection point for the printer cartridge attachment plates 13 (see FIG. 3A). In this embodiment of a 3D printer, print cartridge 1 is stationary along the z-axis and elevating floor 107 moves up and down on z-axis support rod 106.

A print head can operates as a syringe pump and slowly works to extrude the material printing. A powder that is mixed with additives can be loaded into the print head. The syringe pump can act as a piston to push out a heated polymer with additives. The piston could push material which is in a container on the print head. The walls or container portion of the print head can hold the material. One embodiment could have multiple heating elements in this syringe pump/piston to aide in the pre-heating of material for a more even melt-flow/extrusion. One embodiment can be a modular cartridge that can be filled with material which can be pushed by the motor. The pressurized and modular nature of the system can have several advantages. A more pressurized system can operate at lower temperatures. Powders can be mixed in small batches as needed. Powders can be loaded into modular cartridges and printed into a construct.

This type of a print head may need a single or plurality of heaters as well as mixing element to keep additives mixed as uniformly as possible. One embodiment could be prefilled powder cartridges. Another embodiment could be prefilled powdered cartridges that have not only been mixed but heated and to solidify the materials into a block that can then be heated upon the extrusion of printing. It should be noted that a plurality of heaters may operate on different temperatures. One reason that the temperature of 3D printers must be so high is to ensure a rapid transition to a temperature that allows for a meltflow of the polymer to occur quickly enough to print at a reasonable speed. Having a way to pre-heat a polymer to higher temperature can assist this process. For example a gentamicin/polymer powder mixture pre-heated in the canister to 90 C can be more rapidly heated at the extrusion point to the 150 C to 200 C temperature needed in the process. This can allow for a lower temperature to be used in the printing process. A print head may need to have a plurality of heating or mixing elements within it to create a consistent distribution of additive when printing.

Figure 7:
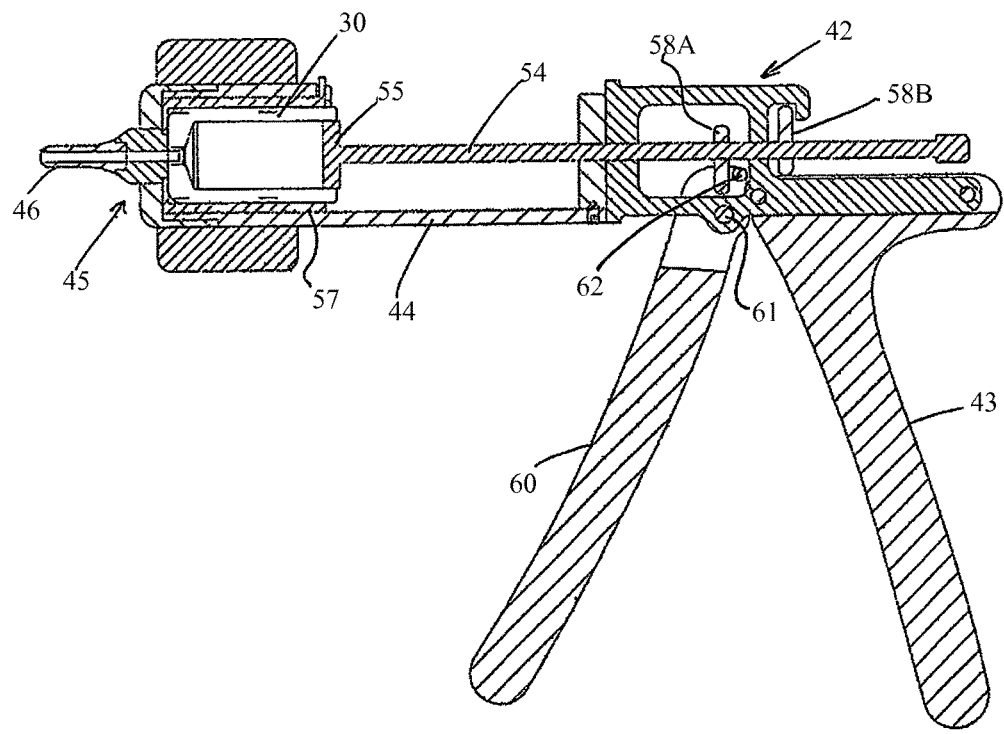
FIG. 7 illustrates a cross-section of the FIG. 5 extruder device.
Figure 8:
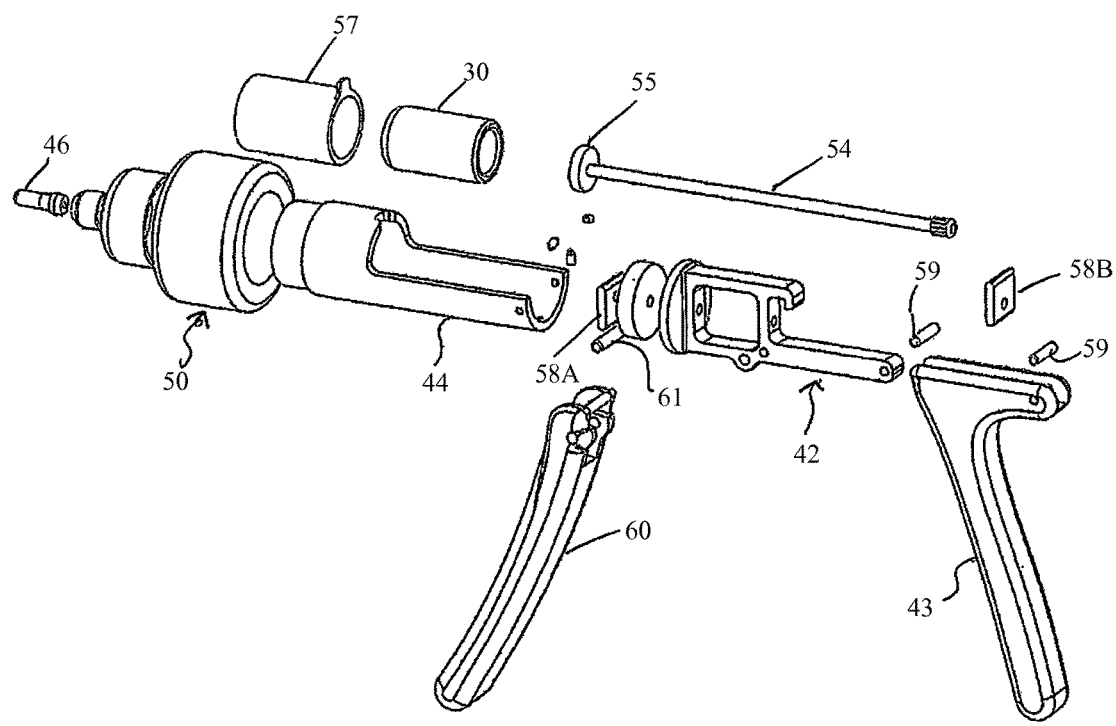
FIG. 8 illustrates an exploded view of the FIG. 5 extruder device.

FIGS. 5 to 8 illustrate another embodiment of the invention, extruder device 40. This example of the extruder device is a hand-held device or extruder "gun" 41. Extruder gun 41 generally comprises the frame 42, which includes the handle portion 43. Also attached to frame 42 is the barrel 44 and attached to barrel 44 is the nozzle assembly 45. As best seen in FIG. 8, approximately two-thirds of the upper half of barrel 44 is open to accommodate the loading of capsule 30 as explained below. The distal end of nozzle assembly 45 will include a small tubular guide tip 46 to help more precisely place semi-flowable materials exiting the extruder gun 41. In this embodiment, heating element 50 is a hollow cylindrical ceramic type heating element. The exploded view of FIG. 8 most clearly shows the plunger 54 with plunger head 55. FIG. 8 also shows the capsule 30 which will contain the substance to be extruded (e.g., a polymer/bioactive agent mixture). FIG. 7 most clearly illustrates how capsule 30 is positioned within barrel 44 such that it may be engaged by the plunger head 55. The capsule spacer 57 (see FIG. 8) may be positioned between the barrel's inner diameter and capsule 30. The lever 60 is pivotally mounted on frame 42 by pivot pin 61.

FIG. 18 shows one embodiment of a capsule 30 which could be employed in the extruder gun 41. Capsule 30 has a body 33 formed of a material such as Pyrex®. An outlet 32 is formed at one end of body 33. In the illustrated embodiment, adhesive aluminum film covers 34A and 34B are positioned over the ends of body 33 to isolate the capsule contents from the outside environment. FIG. 19 suggests how many capsules 30 could be stored in a case 35 having a series of pockets 37 to receive the individual capsules. A cover 36 having a similar series of pockets (hidden from view in the figures) would fit on case 35 and enclose the capsules. In many embodiments, the different capsules 30 in case 35 could contain different combinations of extrudable materials and bioactive agents.

As seen in FIG. 7, capsule 30 (together with spacer 57) is dropped into the upper open area of barrel 44 and urged into the portion of the barrel surrounded by heating element 50. It can be envisioned from FIG. 7 how the plunger 54 is moved forward against capsule 30 by the lever 60 positioned on handle 43. As lever 60 moves toward handle 43, a pin 62 on the upper end of lever 60 pushes ratchet member 58A forward. Ratchet member 58A in turn urges plunger 54 forward when lever 60 moves toward handle 43, but ratchet member 58A may slide rearward on plunger 54 when handle 43 is released. Nevertheless, ratchet member 58B will prevent plunger 54 from moving rearward when force from ratchet member 58A is released. Rotation of plunger 54 disengages the plunger rod from the ratchet members when it is desired to move plunger 54 rearward. The operation of extruder gun 41 is somewhat similar to the printer cartridge described above. The plunger moving forward against capsule 30 forces the extrudable material, raised to its melt flow temperature by heating element 50, into the nozzle assembly 45. As the extrudable material exits guide tip 46, the user holds the guide tip on or adjacent to the surface on which the extrudable material is to be applied.

Another embodiment of the invention is the extruder capsule itself. This embodiment would generally comprise a tubular body with one end of the tubular body configured to collapse inwards when engaged by the plunger. A mixture comprising a setting agent and a bioactive agent as described herein is positioned within the capsule. This capsule could contain a plurality of mixing or heating elements for the components within. The capsule could be filled with powders or a material of variable viscosity. One example would be a pre-formed glue gun stick that already had uniformity of mixing and then was pre-molded. This could be done inside of the cartridge with pre-heating or before loading. The items placed inside the cartridge or cartridge itself could also be sterilized if necessary.

Another embodiment is a brachytherapy seed which will generally include a radioactive seed core and a biocompatible retaining structure connected to the seed core, for example connected to the seed core by being 3D printed onto the seed core. Maintaining position of a brachytherapy seed in the correct location in the body can be challenging. It is possible to use additive manufacturing methods to create end caps or capsules into which the seed may be placed. These end caps can have hooks or rough surfaces of many types that can maintain placement within an area of the body. These end caps/capsules/constructs can be manufactured before placement into a patient or in situ. The materials for these casings can be of any polymer and include biodegradable compounds. These polymers can also be resistant to degradation for permanent structure. Metals and ceramics could also be used for a preferred structure.

In one example (example 1), end caps with a rough surface are placed onto a brachytherapy seed to maintain placement within the prostate by a radiation oncologist, interventional radiologist, surgical oncologist or robotic surgeon. These end caps are made using a biodegradable polymer with an additive manufacturing method.

In another example (example 2), a small capsule that screws together is made to hold a seed. The capsule has rough surfaces and or a circular loop that allows it to be sutured and secured onto a given location of the body. Creating capsules with retractable attachment mechanisms such as hooks or barbs that only spring or move outwards after placement/on command could also be desirable.

It should be noted that advantages to additive manufacturing over injection molding could be substantial. These include the ability to create honeycomb structures or windows or pores throughout a construct to allow greater radiation emission, radiation absorption, drug elution or drug absorption. The percent fill and custom design can allow for more personalized medical treatments.

The structures can be printed directly onto or around the seeds placed onto a platform. Advantages to printing directly onto a seed include a tighter fits and adhesion if a material such as the melt flowing polymer onto the surface of the brachytherapy seed is used. An alternative option is that a print can be paused while seeds are inserted into them. The ability to pause an additive manufacturing process and place components inside constructs can be seen in the 3D printing of motors where a shell is made but heavy metal components are placed by human hand or a robotic surgical arm into position as needed. An advantage of this method is securely locking a seed into place inside the construct with no ability to remove it.

The end cap, capsule or construct can take many forms. Examples could be a screw shape or organic shape to fill a bone defect, such as an area of bone erosion from osteomyelitis or osteosarcoma (or treatment modalities related to these pathologic entities). A screw with a cavity for a seed could anchor the seed in the bone. A screw could be made out of polymers, metal or ceramic materials with windows or honeycomb structure to control dosing. The usage of absorbable polymers or metals such as magnesium screw materials could allow for bone to regrow in a greater area.

One example of using a screw with a seed placed in a distal tip cavity could allow for a later retrieval of the seed as a permanent screw is removed. There would even be the possibility to use a hollow custom rod or screw to allow for the removal and replacement of a seed. If a portion of the screw or rods sticks out of the body a seed can be replaced by a minimally invasive or surgical method.

Screw type shapes of materials could anchor into the prostate and merely require slightly larger gauge needles for insertion.

One example of controlling radiation dosing with custom shells would be to use laser sintering to form a metal shell with a window. The window could have a set degree range. A window with a 180 degree range could be placed facing the interior of a target area of tissue while the solid metal portion could be placed against muscle or nerves to limit exposure. A shell could be made in a needed way and with a material such that radiation emission can be blocked or lessened in one portion and directed or strengthened through another. Rough surfaces or locking a seed and capsule in place with a special suture loop area could prevent movement and rotation of the capsule.

A construct of organic shape can also be made to hold a seed. This could be in the shape of a removed prostate or organic space filling construct and have seeds placed inside it. This could assist with radiating remaining tissue.

Currently small catheters can be used for breast brachytherapy treatment. One embodiment of novel use of 3D printing technology could be to make custom shields of plastics or metals that clip onto these catheters. A shield that covered 180 degrees of the catheter could direct radiation down into the tissue and protect the dermis for dermal/scare salvage.

It was previously noted that capsules could be printed directly onto a brachytherapy seed. The ability to lay polymers on brachytherapy seeds has been confirmed by the Weisman Laboratory group using FDM printers.

It is possible to create 3D printing filaments for FDM printers that contain bioactive molecules, metals or other nanoparticles. These can be printed onto seeds directly. These types of filaments can be done singularly or in combination to obtain a desired result. We incorporate by references the provisional patent filings by Weisman et al. on this topic No. 62/042,795 titled Methods and Devices For 3D Printing or Additive Manufacturing Of Bioactive Medical Devices and Shielding; as well as 62/035,492 Methods and Devices For 3D Printing or Additive Manufacturing Of Bioactive Medical Devices.

The ability to coat a brachytherapy seed in a material that releases a chemotherapeutic agent, a radio-sensitizer or material that shields a portion of the seed could be desirable for usage in a range of medical treatments. This layering can be done in multiple combinations as needed.

For example brachytherapy seeds can be coated in a bioplastic type material that releases methotrexate. A seed could also be coated on one side with a bioplastic containing a radio-sensitizer or shielding material such as barium to lower emission on one side. Combinations of coatings could be done to obtain a desired effect. The material used could be permanent or a bioplastic that degrades in the body.

One alternative method of additive manufacturing could be to dope a 3D printing filament in the case of FDM or material in other printing methods with a radioactive compound. This compound could be printed to create an additively manufactured seed. This could be done with powders in the case of sintering. The seed could be made of permanent or adsorbable material. Other 3D printing methods may require loading and/or doping differently.

For example, a FDM 3D printing filament could be laden with Iodine 125. A material could be used which does not dissolve until the Iodine is mostly inert. Natural body processes would then remove the iodine. A custom implant of any desired size or shape could be made.

Percentage doping of the material could be highly variable. The percentage would relate to the desired radiation dosage and half-life of the material. Wide range of doping percentages may be used and are only constrained by the desired radiation dosage and ability of the material that has been doped to maintain shape.

A bioplastic based seed could be manufactured that was doped with a radioactive additive. This seed could then be placed in a shell or construct. A shell or construct could also be created around or with the seed using additive manufacturing processes. The construct options discussed above provide several options. An entire construct could be organically shaped, made of degradable materials and have a radioactive core.

One example would be FDM 3D printed iodine 125 containing seed. The seed is then coated with bioplastics containing singularly or in combinations of chemotherapeutic agents, radio sensitizers or shielding components.

It should be noted that several additive-manufacturing methods could be used to make custom shaped seeds or constructs to deliver treatment. The standard roughly 0.8 mm by 4.5 mm seed of a cylinder shape may not have to be used with these processes. A thinner/wider, longer/shorter etc. . . . seed or alternative to cylinder shape could be made alone or within a construct to customize the radiation dosage for personalized forms of treatment.

One possible alternative embodiment may be to use a print pen to lay down a material containing a doped percentage of radioactive material to a site or margins of excised tissue. The material may be laid down by human hands or robotic arms in a surgical procedure or by instrumentation in a minimally invasive procedure. A removed bone defect in the case of osteosarcomas may be filled.

For example a doped filament with a radioactive material is used with a print pen or gun to mark the margins of a removed tumor. The pen may have to layer the material or have multiple cartridges as it is used to make sure the radioactive material is incased in a shell.

One embodiment of this method may be the extrusion of a thin polymer filament that has been doped with a radioactive additive. This filament could be used as suture to mark an area within the body or sew the material its' self into a location. This suture may need to be coated in a shielding or other material to direct the radiation emissions. The material could be any type of polymer either adsorbable or otherwise.

It is also possible to use proteins or more thermally sensitive biological additives. A spray coating can be done to these constructs before implantation when they are not at thermal degradation points. Alternatively a special print head can be used to spray or lay additives onto the construct as it is printing a layer but after the process is thermally suitable. One embodiment of this machine would be having multiple print heads lay down multiple components of a construct at the same time.

Small microspheres, nanoparticles or larger particles of a radioactive material could be laid down onto the construct as it was being made. This could allow for portions of the construct to be radioactive while others are not.

In other examples, additive manufacturing of custom catheters or needles may be needed for custom construct placement. Additive manufacturing of custom sutures, staples, or meshes may be needed for custom construct securement to different areas of the body. Alternatively, an insert that is bioactive could be a staple, hook, spear or anchoring device.

For example, 3D printer filament can be made out of PLA bioplastics that have been mixed with antibiotics, chemotherapeutics or antiseptics. The plastic pellets are mixed with a powdered bioactive reagent and then extruded at proper temperature to yield a printable filament. This filament is then printed on a fused deposition modeling 3D printer. The printed object can be an antibiotic bead, drug eluting catheter or any printable medical device, however the extrusion and printing temperature must not exceed the denaturing temperature of the additive.

In another example embodiment (example 3), PLA pellets were run through a filament extruder with 2% gentamicine powder at 175 Celsius. The resulting filament was tested on bacterial plates using antibiotic susceptibility gel diffusion testing using *E. Coli* bacteria. A kill zone was observed around the filament. A broth culture also showed no bacterial growth when tested with the same filament. The filament is run through a 3D printer head nozzle at 220 Celsius and 300 um fibers are created. The fibers are then plated and also showed a kill zone or no bacterial growth on a plate or broth culture.

To the extent that the above example does not yield a sufficiently uniform dispersion of gentamicin throughout the entire filament, the filament can be chopped up and re-extruded for better mixing. This adds additional heating to the bioactive reagent, and could cause additional degradation of the substance of interest for each subsequent extrusion. A more optimal approach would be a uniform amount of antibiotic or bioactive reagent coating each pellet or a smaller pellet or powdered plastic that can be uniformly mixed.

The pellet size for PLA & ABS plastics can vary from differing manufacturers. Many manufacturers utilize pellet sizes ranging from 2-4 mm, however larger and smaller pellets can be found. Powders (e.g., particles can be reduced to nearly any size desired) of these plastics can also be obtained. Should coating be utilized for the dispersion of additives, smaller pellets or powders are preferable as this provides greater surface area, which in turn provides more uniformity in dispersion. Pellets can be ball milled or, using a grinder, ground into powders. There are also chemical methods to dissolve the plastics into smaller powdered pieces.

The elastic nature of many of these powders can make milling or grinding difficult. This can be solved by cryo or freeze fracturing, freeze milling or freeze grinding. Liquid nitrogen or a low temperature setting can be used to allow the material to be easily shattered into smaller sizes. An example of this could a cryo-mortar and pestle. PLA scraps can also be used instead of pellets. A strong enough grinder or mill can operate at higher temperatures but normally optimal performance can be achieved by lowering the temperature of a plastic to below the ductile-brittle transition temperature of the plastic to enable shattering of the material. These finer powders plastics or polymers can be uniformly mixed with an antibiotic or other suitable bioactive reagent for filament extrusion.

In another example (example 4), PLA plastic pellets were cryo-mortar and pestled into a fine powder. They were then mixed with 2% gentamicin by weight and that filament was extruded at 175 Celsius. The resulting filament is tested on bacterial plates using antibiotic susceptibility gel diffusion testing using *E. Coli* bacteria. A kill zone was observed around the filament. A broth culture also showed no bacterial growth when tested with the same filament. The filament was run through a 3D printer head nozzle at 220 Celsius and 300 um fibers were created. The fibers were then plated and also showed no bacterial growth on a plate or broth culture.

It should be noted that a traditional filament extruder could at times have difficulty with fine powders. They can cause clogs or if sufficient back pressure to feed the system is lacking, flow into the auger system can be hindered. A piston based extrusion system instead of an auger can overcome some of these challenges by providing greater back pressure to the feedstock within the system. Powder can be loaded, heated and then pushed out of the pipe and through the die. The need for a piston would depend on the type of material used. In certain circumstances, piston based extruders may be disadvantageous since they could not as easily extrude large continuous amounts of filament as the auger systems do. In the case of bioactive filaments, small batch manufacturing or a few feet of filament at a time would be sufficient for these systems to become desirable.

As a further example (example 5) Bosworth PMMA fine powder that is almost uniformly spherical microspheres were extruded using an auger based system with no difficulty into a 1.75 mm diameter filament at 230 Celsius. The filament was then 3D printed into discs. The cyto-toxicity of the PMMA only filament was tested with osteosarcoma cells. Upon an XTT assay The PMMA extruded filament had no toxic effect on the cells with higher activity than a control well. A low viscosity Orthowright bone cement of PMMA mixed with MMA was put in a syringe with a roughly 1.75 mm extrusion point and a filament was made. The low viscosity Orthowright filament had high toxicity upon XTT assay.

It should be noted that almost any off the shelf bone cement from manufacturers including but not limited to Orthowright and Stryker can have the powdered component extruded at proper melt flow temperatures into a filament. The filament can have any desired additive that the necessary extrusion temperature will not unnecessarily degrade. The improvement is the lack of the liquid monomer or toxins needed to catalyze a standard reaction to make the bone cement. PMMA powder with additives including but not limited to barium and antibiotics can be fabricated into a 3D printing filament. Printing of PMMA based filaments into antibiotic beads is easily possible. However, they would still be surgically removed at some point since they do not degrade. An advantage bioplastics or absorbable polymers would have over PMMA would be a lack of a need to surgically remove them at a later date. 3D fabrication can have additional surface area for enhanced elution and less rough surfaces that can damage tissue or break off when compared to traditional antibiotic bead hand manufacturing.

There are methods that allow for uniformity in the usage of traditional 3 mm or other larger/smaller sized injection molding pellets or granules by coating a similar amount of additive substance on each pellet. A high temperature coating oil like silicone Dow Corning 747 oil or a similar oil (sometimes referred to herein as an "adhering agent") can be used to coat the pellets or granules. The pellets can then be vortexed for a uniform coating. After oil coating, the pellets should be transferred to a new container. This is to avoid coating the lumen of the container holding the pellets with the additive, losing fidelity of the doping percentage. A powder of a bioactive agent can then be added and vortexed with the oil coated pellets. A uniform coating will appear on each bead. It is important to note that a proper amount of oil must be used for the sample of pellets. Too much will cause clumping of the pellets. Too little will leave excess powder on the bottom of the tube. Too much oil can also cause a bubbling or warping of the final filament. If too much warping occurs the filament will not feed easily into the 3D printer.

In a further example (example 6), 20 grams of PLA pellets were added to a 50 mL sterile plastic tube. 20 uL of DC 747 silicone oil was added and the tube was vortexed until the beads were uniformly coated. The beads were then placed in a new 50 mL sterile plastic tube. To make a 1% coating, 200 mg of gentamicin powder was added to the beads and subsequently vortexed. The coated beads were then added to a filament extruder, and a 1.75 mm filament that was 1% gentamicin was produced. The filament was used to produce 3D printed squares, 5 mm diameter discs, 6 mm diameter spherical beads with a 3 mm hole, and catheters (14 french single hole) on a Makerbot 2X printer. They were then tested on bacterial plates and broth cultures showing successful kill zones and no growth in broth.

Depending on the size of the pellet, the available surface area for coating has its geometrical limits. A way to add additional powders is to use a layer-by-layer coating method. Using the coating process found in example 6, additional layers of oil and additive can be added alternatively to achieve greater final doping percentages. Issues can arise, however, by the addition of too much oil leading to extrusion complications as described in above paragraph.

In another example (example 7), optimal coating amounts per layer for the ExtrusionBot filament extruder device to prevent clumping for 20 gram pellet batches ranged from 1 uL to 100 uL depending on the gentamicin, halloysite, methotrexate, tobramycin or iron powder additives. It should be noted that the 20 gram sample size and 1 uL to 100 uL range is not limiting and that lower or higher pellet or coating amounts can be used as the materials and desired results dictate.

The silicone oil method is not the only coating method that can be used. In addition to coating oils, a water coating method can be used by lightly wetting the beads if the bioactive substance is not highly soluble. This can work with nitrofuratonin or methotrexate.

A novel nebulizer or atomizer based method can also be used to coat the pellets. An additive can be dissolved or suspended in solution. Gentamicin is highly soluble in water. Methotrexate can be suspended in water but is more highly soluble in DMSO. The proper solvent for the desired additive should be selected. A desired solution of additives can then be loaded into a nebulizer and connected to a container of beads. An alternative setup could be a syringe placed on a syringe pump that is connected to an atomizer. The atomizer could then be positioned to coat pellets.

Example of one embodiment: 6) A syringe was loaded with 5 ml of a solution comprising deionized water and 500 mg of gentamicin. 20 grams of PLA pellets were placed into a double neck Erlenmeyer flask. An atomizer was placed into the vertical neck opening. The syringe was placed into a syringe pump and placed connected to the atomizer via the horizontal neck opening on the flask. The syringe pump was run at 0.1 mL per minute until the syringe was empty and the solution coated the PLA pellets. The flask was placed on a heating platform set to 50 Celsius to aid in evaporating any excess water or solution which reached the bottom of the flask. After coating and drying, the beads were run through an extrusionbot filament extruder at 175 Celsius to make a 1.75 mm filament. The filament was printed on a Makerbot 2X 3D printer. Filament and test discs were run with *E. coli* plates and broths. The plates exhibited zones of inhibition and the broth cultures showed no *E. coli* growth compared to controls.

These small batch processes can be scaled up using more traditional extrusion techniques. One skilled in the art of industrial extrusion would be able to set the necessary parameters for fabrication.

It should be noted that temperature optimization is a consideration in manufacturing filaments and 3D printing filaments with bioactive agents. Different compounds have unique melting points and degradation temperatures (i.e., the temperature beyond which the bioactive agent's therapeutic effect is significantly reduced). They also react differently with plastics or polymers which can change release profiles. The Sigma Aldrich MSDS on Gentamicin Sulfate Product Number G 1264 CAS Number: 1405-41-0 has a melting point of 218 to 237 Celsius. The melting point on tobramycin varies in multiple sources but was seen in the 160 to 170 Celsius range. In many embodiments, the setting agent and bioactive agent are a paired such that the melt flow temperature of the former does not exceed the degradation temperature of the latter. It should be noted that degradation temperatures can be exceeded for brief amounts of time without effecting all bioactivity.

Example of one embodiment: 7) Gentamicin and Tobramycin were heated in a Vulcan oven to 220 Celsius for 5 minutes. The tobramycin melted while the gentamicin did not. The antibiotics were tested against control uncooked powders in 1 mg amounts for activity in both broth and bacterial plate culture. Both cooked and uncooked of both gentamicin and tobramycin were biologically active. The plates had kill zones and the broth cultures had no bacterial growth. Using a silicone coating method noted above and in 20 gram batches, filaments were then extruded of both 1% and 2.5% amounts of either gentamicin and tobramycin. This was done at 175 Celsius using an Extrusionbot filament extruder. The tobramycin melted and "bonded" with the PLA bioplastic causing a silver colored filament. Noting this effect an additional tobramycin filament was extruded at 150 Celsius which did not cause a melting and bonding of tobramycin to the PLA material. The filaments were 3D printed into discs at 220 Celsius using a makerbot 3D printer. Gentamicin filaments and discs showed strong kill zones comparable or better than bone cement filaments and discs with the same amount of gentamicin in both bacterial plate and broth cultures. Tobramycin extruded at 175 Celsius showed minimal bacterial inhibition on bacterial plates and most broth cultures showed bacterial growth. This result was less than that displayed by tobramycin bone cement controls. Tobramycin filament extruded at 150 Celsius showed stronger inhibition on bacterial plates and in broth cultures.

It should be noted that the material properties of the plastics or polymers have different effects when combining with additives in controlling drug elution or release. Certain plastics may be more porous or allow for more optimal release in a certain situation than others while some plastics may react to or bond with an additive to inhibit release.

Another example (example 10), using a 1% silicone coating oil method, methotrexate was added to PCL beads and extruded at temperatures ranging from 90 to 150 Celsius. The PCL filament was added to Osteosarcoma assays and setup for a 24 hour elution profile. Using a 2.5% silicone coating oil method, methotrexate was added to PLA beads and extruded at 150 Celsius. The PLA filament was added to osteosarcoma assays and setup for a 24 hour elution profile. The PCL elution profile existed but was minimal while the PLA filament had a substantial elution profile. The PLA cell culture plate had a substantial inhibition of osteosarcoma cell growth while the PCL cell culture plate showed a much more minimal inhibition of the cancer cells.

Certain additives can be used to enhance elution profiles or material properties. Halloysite nanotubes or other nanoclays as noted in the Mills' patent application listed above can increase the pore size of the plastics. They can also be loaded with additives for a controlled or extended release.

A further example (example 11), using the silicon oil coating method 1% or 10% by weight, halloysite nanotubes were added to both PLA and ABS pellets. Filaments were created using an extrusionbot filament extruder at appropriate temperatures for the plastics to yield a 1.75 mm diameter filament. Pore size was tested using a quanta-chrome nova 2200e surface analyzer. Filaments with HNTs were found to have an increased pore size. The filaments were tested on bacterial plates and broth cultures. Both showed no signs of antimicrobial activity. HNTs were then loaded with gentamicin. Gentamicin was dissolved in water at 100 mg per ml. Then 250 mg of HNTs were added to each mL. Loading was done in 10 mL batches. The dried and washed Gentamicin loaded halloysite were then added to PLA pellets using a silicone layer-by-layer coating method to reach a 7.5% coating. This would result in a roughly 0.75% to 1% gentamicin content in the filament based upon HNT loading capabilities. The filament was then used to print 6 mm diameter antibiotic beads. The filament and beads were then plated on bacterial plates and in broth cultures. All plates showed a kill zone and all bacterial broth cultures showed no or substantially reduced bacterial growth after 24 hours.

It should be noted that combinations of different antibiotics can enhance release profiles. A filament that contains an insoluble antibiotic mixed with a highly soluble one can yield a burst release profile while maintaining an antimicrobial plastic. Additionally, halloysite nanotubes or similar nanoclays and controlled release technology can be mixed with combinations of antibiotics to allow for a desired release profile.

In another example, (example 12), a 1% nitrofuratonin antibiotic PLA filament was created using a silicone coating oil method. The filament showed antimicrobial properties on bacterial plates but did not kill the broth cultures. Given the high solubility of gentamicin, it would release in a burst from a filament or 3D printed construct. Nitrofuratonin gave plastic antimicrobial capabilities. Combinations of soluble and insoluble antibiotics can leads to longer acting antimicrobial activity. It should be noted that these combinations can include but are not limited to HNTs or nanoclays (loaded/unloaded), antiseptic or any other additive compound that can be 3D printed.

We note that the Mill's patent and publication number WO 2014075185 A1 (which is incorporated by reference herein) and the references they cite provide examples of antibiotics, plastics, antiseptic and other biological compounds which may be employed with the techniques described herein.

Nonlimiting examples of the polymer stock material may include various thermoplastic polymers and/or free radical polymers and/or cross-linked polymers. For example poly (methyl methacrylates), acrylonitrile butadiene styrenes, polycarbonates, blends of acrylonitrile butadiene styrene(s) and polycarbonate(s), polyether ether ketones, polyethylenes, polyamides, polylactic acids, polyphenylsulfones, polystyrenes, nylon particularly nylon 12, among others. Also useful are methylmethacrylates, polylactides, polyglycolides, polycaprolactones, polyanhydrides, polyamines, polyurethanes, polyesteramides, polyorthoesters, polydioxanones, polyacetals, polyketals, polycarbonates, polyorthocarbonates, polyphosphazenes, succinates, poly(malic acid), poly(amino acids), polyvinylpyrrolidone, polyethylene glycol, polyhydroxycellulose, polysaccharides, chitin, chitosan, and copolymers, block copolymers, multi-block co-polymers, multi-block co-polymers with polyethylene glycol (PEG), polyols, terpolymers and mixtures thereof. Additional plastics could be polypropylene, allyl resin, ethyl vinyl acetate, polyvinyl chloride, polyvinyl alcohol, epoxy, ethylene vinyl alcohol, acrylic, silicones, elastomers, ionomers, polyamide-imide, polyisoprene, polystyrene, polysulfone polycarbonate, polyoxymethylene, polyarkyletherketon, polytetrafluoroethylene, polyetherketone, polymer foams, and other polymers.

There are many different abbreviations and slight modifications to many of the polymers listed in the preceding paragraphs. More information on many of them such as PLLA, PLDLA, Biodegradable AB Diblock Copolymers, Biodegradable ABA Triblock Copolymers, Biodegradable Block Copolymers, Lactide and Glycolide Polymers, Caprolactone Polymers, Chitosan, polysaccharides, linear polysaccharides, glycosaminoglycans, proetoglycans, lipoproteins, Hydroxybutyric Acids, Polyanhydrides and Polyesters, Polyphosphazenes, Polyphosphoesters Natural Polymers and Biopolymers can be found listed on the Sigma Aldrich biopolymer catalog updated August 2014 and in the following sources and references they cite: 1. Zhang, X. et al. *J.M.S.-Rev. Macromol. Chem. Phys.*, C33 (1), 81 (1993). 2. Piskin, E. *J. Biomater. Sci. Polym. Ed.*, 6, 775 (1995). 3. Shalaby, S. W. *Biomedical Polymers*; Hanser: New York (1994). 4. Uhrich, K. E. et al. *Chem. Rev.*, 99, 3181 (1999). 5. Dobrzynski, P. et al. *Macromolecules*, 32, 4735 (1999). 6. Bioabsorbable materials in orthopaedics Acta Orthop. Belg., 2007, 73, 159-169 By Kontakis, all on which are incorporated by reference herein.

The bioactive agents may include metals, proteins, peptides, polypeptides, sugars, antimicrobials, antiseptics, chemo-therapeutics, carbohydrates, lipids, hormones, minerals, and vitamins, and radio-active agents. The term "antimicrobial" as used herein means antibiotic, antiseptic, or disinfectant. Classes of antibiotic compositions that may be useful for in the methods of the present disclosure for producing filaments and then antimicrobial implantable medical devices include aminoglycosides exemplified by tobramycin, gentamicin, neomycin, streptomycin, and the like; azoles exemplified by fluconazole, itraconazole, and the like; f3-lactam antibiotics exemplified by penams, cephems, carbapenems, monobactams, f3-lactamase inhibitors, and the like; cephalosporins exemplified by cefacetrile, cefadroxyl, cephalexin, cephazolin, cefproxil, cefbuperazone, and the like; chloramphenicol; clindamycin; fusidic acid; glycopeptides exemplified by vancomycin, teicoplanin, ramoplanin, and the like; macrolides exemplified by azithromycin, clarithromycin, dirithromysin, erythromycin, spiramycin, tylosin, and the like; metronidazole; mupirocin; penicillins exemplified by benzylpenicillin, procaine benzylpenicillin, benzathine benzylpenicillin, phenoxymethylpenicillin, and the like; polyenes exemplified by amphotericin B, nystatin, natamycin, and the like; quinolones exemplified by ciprofloxacin, ofloxacin, danofloxacin, and the like; rifamycins exemplified by rifampicin, rifabutin, rifapentine, rifaximin, and the like; sulfonamides exemplified by sulfacetamine, sulfadoxine, and the like; tetracyclines exemplified by doxycycline, minocycline, tigecycline, and the like; and trimethoprim, among others. It is expected that tobramycin and/or gentamicin and/or neomycin and/or vancomycin are particularly suitable for concurrent deposition with polymeric materials for additive manufacturing of the antimicrobial medical devices of the present disclosure. The above list does not list all potential antibiotics and substances and is not all inclusive.

It should be noted that virtually all appropriately temperature stable antiseptics such as betadine powder can be used to make filaments. These include, but are not limited to, palcohols including ethanol, 1-propanol and 2-propanol/isopropanol or mixtures or stand alone compounds of tincture of iodine, benzalkonium chloride, chlorhexidine, octenidine dihydrochloride; quaternary ammonium compounds including benzalkonium chloride, cetyl trimethylammonium bromide, cetylpyridinium chloride, benzethonium chloride, chlorhexidine, and octenidine; boric acid;

brilliant green; chlorhexidine gluconate; hydrogen peroxide; iodine; manuka honey; octenidine dihydrochloride; phenol; hexachlorophene; polyhexanide. Antiseptics in addition to chemotherapeutics could be particularly valuable to custom print surgical ports to prevent cancer seeding during surgeries. Metal ions such as silver can also act as antiseptics. The above list does not list all potential antiseptics and substances and is not all-inclusive.

It should be noted that many biological proteins would be denatured by the heating process and destroyed (i.e., the proteins degradation temperature is exceeded). If a low enough melting temperature or similar plastic process is found then it is possible to use proteins as listed in WO 2014075185. For example, bone morphogenic protein can be stable for short time periods at 70 Celsius while PCL melts at 60 Celsius, Clin Orthop Relat Res. 2001 September; (390):252-8. The effect of heat-treated human bone morphogenetic protein on clinical implantation. Izawa Hl, Hachiya Y, Kawai T, Muramatsu K, Narita Y, Ban N, Yoshizawa H. It should also be noted that the high cost of proteins could make mixing with beads prohibitively expensive. More targeted atomizer based spray coatings or mixing with coating oils would still work. However, there is a method to allow fabrication of plastic prints with proteins without denaturing proteins with lower melting points as well as likely more affordable. If a spray apparatus similar to an atomizer that can be directed on the filament leaving the 3D printer print head at a point that the plastic has cooled enough to not denature the protein then the layer-by layer nature of the print can be coated. The plastic may be "sticky" enough after heating to bind the proteins without denaturing them. An alternative method could be to briefly pause the print and spray each layer of the construct after it has sufficiently cooled. In the case of PCL noted above while it melts at 60 Celsius the melt flow is more appropriate for 3D printing at 160 Celsius. However, the PCL material is still "sticky" and able to collect and hold bone morphogenic protein at 60 Celsius which is below the proteins decomposition temperature. Another method would be through the use of rapidly cooling plastics such as polylactic acids that only retain their heat for a short period of time, and as such, after leaving the extrusion chamber or the 3D printing head, rapidly lose any excess temperature, returning quickly to room temperature. This method limits the heating time of any additives, leading to a greater preservation of biological agents.

The fabrication of filaments with chemotherapeutic properties would have great utility. The following chemotherapeutic drug list is not inclusive but lists many of the existing drugs from a National Cancer Institute list from drugs approved for conditions related to cancer updated Aug. 16, 2013 and lists: Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Adrucil (Fluorouracil), Afatinib Dimaleate, Afinitor (Everolimus), Aldara (Imiquimod), Aldesleukin, Alemtuzumab, Alimta (Pemetrexed Disodium), Aloxi (Palonosetron Hydrochloride), Ambochlorin (Chlorambucil), Amboclorin (Chlorambucil), Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase *Erwinia chrysanthemi*, Avastin (Bevacizumab), Axitinib, Azacitidine, BEACOPP, Becenum (Carmustine), Beleodaq (Belinostat), Belinostat, Bendamustine Hydrochloride, BEP, Bevacizumab, Bexarotene, Bexxar (Tositumomab and I 131 Iodine Tositumomab), Bicalutamide, BiCNU (Carmustine), Bleomycin, Bortezomib, Bosulif (Bosutinib), Bosutinib, Brentuximab Vedotin, Busulfan, Busulfex (Busulfan), Cabazitaxel, Cabozantinib-S-Malate, CAF, Campath (Alemtuzumab), Camptosar (Irinotecan Hydrochloride), Capecitabine, CAPDX, Carboplatin, CARBOPLATIN-TAXOL, Carfilzomib, Carmubris (Carmustine), Carmustine, Carmustine Implant, Casodex (Bicalutamide), CeeNU (Lomustine), Ceritinib, Cerubidine (Daunorubicin Hydrochloride), Cervarix (Recombinant HPV Bivalent Vaccine), Cetuximab, Chlorambucil, CHLORAMBUCIL-PREDNISONE, CHOP, Cisplatin, Clafen (Cyclophosphamide), Clofarabine, Clofarex (Clofarabine), Clolar (Clofarabine), CMF, Cometriq (Cabozantinib-S-Malate), COPP, COPP-ABV, Cosmegen (Dactinomycin), Crizotinib, CVP, Cyclophosphamide, Cyfos (Ifosfamide), Cyramza (Ramucirumab), Cytarabine, Cytarabine, Liposomal, Cytosar-U (Cytarabine), Cytoxan (Cyclophosphamide), Dabrafenib, Dacarbazine, Dacogen (Decitabine), Dactinomycin, Dasatinib, Daunorubicin Hydrochloride, Decitabine, Degarelix, Denileukin Diftitox, Denosumab, DepoCyt (Liposomal Cytarabine), DepoFoam (Liposomal Cytarabine), Dexrazoxane Hydrochloride, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Efudex (Fluorouracil), Elitek (Rasburicase), Ellence (Epirubicin Hydrochloride), Eloxatin (Oxaliplatin), Eltrombopag Olamine, Emend (Aprepitant), Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase *Erwinia chrysanthemi*), Etopophos (Etoposide Phosphate), Etoposide, Etoposide Phosphate, Evacet (Doxorubicin Hydrochloride Liposome), Everolimus, Evista (Raloxifene Hydrochloride), Exemestane, Fareston (Toremifene), Faslodex (Fulvestrant), FEC, Femara (Letrozole), Filgrastim, Fludara (Fludarabine Phosphate), Fludarabine Phosphate, Fluoroplex (Fluorouracil), Fluorouracil, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Herceptin (Trastuzumab), Recombinant, Hycamtin (Topotecan Hydrochloride), Hyper-CVAD, Ibritumomab Tiuxetan, Ibrutinib, ICE, Iclusig (Ponatinib Hydrochloride), Idelalisib, Ifex (Ifosfamide), Ifosfamide, Ifosfamidum (Ifosfamide), Imatinib Mesylate, Imbruvica (Ibrutinib), Imiquimod, Inlyta (Axitinib), Intron A (Recombinant Interferon Alfa-2b), Iodine 131 Tositumomab and Tositumomab, Ipilimumab, Iressa (Gefitinib), Irinotecan Hydrochloride, Istodax (Romidepsin), Ixabepilone, Ixempra (Ixabepilone), Jakafi (Ruxolitinib Phosphate), Jevtana (Cabazitaxel), Kadcyla (Ado-Trastuzumab Emtansine), Keoxifene (Raloxifene Hydrochloride), Kepivance (Palifermin), Kyprolis (Carfilzomib), Lapatinib Ditosylate, Lenalidomide, Letrozole, Leucovorin Calcium, Leukeran (Chlorambucil), Leuprolide Acetate, Levulan (Aminolevulinic Acid), Linfolizin (Chlorambucil), LipoDox (Doxorubicin Hydrochloride Liposome), Liposomal Cytarabine, Lomustine, Lupron (Leuprolide Acetate), Lupron Depot (Leuprolide Acetate), Lupron Depot-Ped (Leuprolide Acetate), Lupron Depot-3 Month (Leuprolide Acetate), Lupron Depot-4 Month (Leuprolide Acetate), Marqibo (Vincristine Sulfate Liposome), Matulane (Procarbazine Hydrochloride), Mechlorethamine Hydrochloride, Megace (Megestrol Acetate), Megestrol Acetate, Mekinist (Trametinib), Mercaptopurine, Mesna, Mesnex (Mesna), Methazolastone (Temozolomide), Methotrexate, Methotrexate LPF (Methotrexate), Mexate (Methotrexate), Mexate-AQ (Methotrexate), Mitomycin C, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Nelarabine, Neosar (Cyclophosphamide), Neupogen (Filgrastim), Nexavar (Sorafenib Tosylate), Nilotinib, Nolvadex (Tamoxifen Citrate), Nplate (Romiplostim), Obinutuzumab, Ofatumumab, Omacetaxine Mepesuccinate, Oncaspar (Pegaspargase), Ontak (Denileukin Diftitox), Oxaliplatin, Paclitaxel, Paclitaxel Albumin-stabilized Nanoparticle Formulation, PAD, Palifermin, Palonosetron Hydrochloride, Pamidronate Disodium, Panitumumab, Paraplat (Carboplatin), Paraplatin (Carboplatin), Pazopanib Hydrochloride, Pegaspargase, Peginterferon Alfa-2b, PEG-Intron (Peginterferon Alfa-2b), Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Pralatrexate, Prednisone, Procarbazine Hydrochloride, Proleukin (Aldesleukin), Prolia (Denosumab), Promacta (Eltrombopag Olamine), Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant HPV Bivalent Vaccine, Recombinant HPV Quadrivalent Vaccine, Recombinant Interferon Alfa-2b, Regorafenib, Revlimid (Lenalidomide), Rheumatrex (Methotrexate), Rituxan (Rituximab), Rituximab, Romidepsin, Romiplostim, Rubidomycin (Daunorubicin Hydrochloride), Ruxolitinib Phosphate, Sclerosol Intrapleural Aerosol (Talc), Siltuximab, Sipuleucel-T, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synovir (Thalidomide), Synribo (Omacetaxine Mepesuccinate), TAC, Tafinlar (Dabrafenib), Talc, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Temodar (Temozolomide), Temozolomide, Temsirolimus, Thalidomide, Thalomid (Thalidomide), Toposar (Etoposide), Topotecan Hydrochloride, Toremifene, Torisel (Temsirolimus), Tositumomab and I 131 Iodine Tositumomab, Totect (Dexrazoxane Hydrochloride), Trametinib, Trastuzumab, Treanda (Bendamustine Hydrochloride), Trisenox (Arsenic Trioxide), Tykerb (Lapatinib Ditosylate), Vandetanib, VAMP, Vectibix (Panitumumab), VeIP, Velban (Vinblastine Sulfate), Velcade (Bortezomib), Velsar (Vinblastine Sulfate), Vemurafenib, VePesid (Etoposide), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, Vismodegib, Voraxaze (Glucarpidase), Vorinostat, Votrient (Pazopanib Hydrochloride), Wellcovorin (Leucovorin Calcium), Xalkori (Crizotinib), Xeloda (Capecitabine), XELOX, Xgeva (Denosumab), Xofigo (Radium 223 Dichloride), Xtandi (Enzalutamide), Yervoy (Ipilimumab), Zaltrap (Ziv-Aflibercept), Zelboraf (Vemurafenib), Zevalin (Ibritumomab Tiuxetan), Zinecard (Dexrazoxane Hydrochloride), Ziv-Aflibercept, Zoladex (Goserelin Acetate), Zoledronic Acid, Zolinza (Vorinostat), Zometa (Zoledronic Acid), Zydelig (Idelalisib), Zykadia (Ceritinib), and Zytiga (Abiraterone Acetate).

For coating of the beads, a fluid with sufficient properties to readily stick to the beads and not cause manufacturing issues when exposed to the extrusion or print temperatures is required. In using this method for biological applications, the coating fluid to be used must also be biocompatible. Examples of coating fluids include, but are not limited to, oils such as silicone or biological oils or biological coating compounds.

The percent of bioactive agent depends greatly on the particular bioactive agent. As nonlimiting examples, many antibiotics would be added in a 0.1% to 25% by weight mixture with the polymer stock material (or any subrange therebetween). However, chemotherapeutics, protein such a growth factors or hormones may have the desired effect at substantially lower concentrations, for example 0.01% or even a lower percentage. Depending on the plastic it may also be possible to mix in percentages far greater than 25% while maintaining strength. Additives such as HNTs or nanoclays which can strengthen plastics could allow for increases in percent mixing. Percentages of antibiotic could also potentially be substantially higher in the sense that the construct is intended to dissolve very rapidly and merely act as a delivery vehicle or "binder" for the antibiotic. This is shown in the paper "Biomed Mater. 2009 December; 4(6): 065005. doi: 10.1088/1748-6041/4/6/065005. A programmed release multi-drug implant fabricated by three-dimensional printing technology for bone tuberculosis therapy. Wu Wl, Zheng Q, Guo X, Sun J, Liu Y," which is incorporated by reference herein. It may be possible to use fine powders in a piston based extruder and for example PCL to create filaments of upwards of 80-90% antibiotic. Percent weight in manufacturing would be determined by desired elution rate, zone of desired effect, desire for elution to have a local or systemic effect or many other variables. The strength and ability for extrusion of the plastic or polymer would also be relevant. Thus, the percentage of bioactive agent may range anywhere from 0.01% to 95% by weight (or any subrange therebetween).

It should be noted that bacterial plates and cultures were carried out as close to Kirby-Bauer ISO standards as possible being that of 100 mm Mueller Hinton plates or Mueller Hinton broths. *E. Coli* colonies (Sigma Aldrich Vitroid Origin) used to seed plates were taken from 0.5 McFarland standard solutions in 50 uL quantities. Control plates and broths were used. Control PLA printed discs, beads, stents and catheters were used to compare against antibiotic filaments. Molded bone cement beads, discs and filaments made of Ortho-Right LV bone cements were used as comparison for no antibiotic and antibiotic controls.

Another embodiment of the invention is a real time scannable and printable method for osteomyletis treatment or tumor margin containment. A 3D scanner can be used to scan a defect in a bone or surgical site. A negative fill or plug of the image can be made. Then, an antibiotic filament or chemotherapeutic filament can be used to print a filler or plug to the hole or site. In addition to the 3D scanner, dimensional information may be obtained by another medical imaging device such as (i) a video image recorder, (ii) a CAT scan machine, (iii) an MRI machine, (iv) a PET scan machine, or (v) an x-ray machine, In a further example, (example 13), a 6 inch section of cow femur was taken and had a hole drilled in it with a 6 mm diameter drill bit to a depth of 3 cm. Additionally, an amorphous shape roughly half an inch with carrying depth was made. A 3D scanner was used to take a scan of both holes. The resulting scan was taken and a negative of the holes were made. The plug or fill of these holes was then printed with a control PLA and 1% gentamicin filament on a Makerbot 5th Generation Replicator printer. The holes were then fit with the plugs. A very good fit was obtained. It should be noted that leaving empty cavities in the human body could lead to complications or infection. This was additionally done with irregularly shaped holes in the cow femur and a scanning device. It should be noted that medical scanning devices which include but are not limited to CT, MRIs, X-rays and video imaging devices could be used to create custom bioactive implants from a patients scans.

One use of these bioactive implants is for filling fractures or punctures in a bone or filling a surgical field, or therapeutically addressing any other anatomical defect or "anatomical condition" which can be added by use for the bioactive implants. An extruder device would have an automated feed system and customizable temperature settings, e.g., a resistance heater to generate heat and a thermistor to regulate it. A hand held extruder device would be used to manually print a plug, fill certain aspects of a site or allow for special drug eluting properties on a site. This could be, for example, the extruder gun describe above in reference to FIGS. 5 to 8.

As another example (example 14), a 6 inch portion of cow femur had holes drilled into it with a 6 mm drill bit. The holes were roughly 3 cm deep. A modified 3D print gun using a Makerbot 3D printer head was created. A 1% methotrexate PCL filament was extruded at 160 Celsius, manually resulting in a fill of the hole using a roughly 300 um filament in a layer by layer fashion. This allowed for cooling of filament and less thermal transfer to the surrounding material. A plug was also filled using a 1% gentamicin filament that was 3D printed at 300 um. The bone defects were filled in both cases.

Additive manufacturing methods such as 3D printing utilize computer-aided manufactured to the manufacturing device. As such, any shape can be conceivably made through this method assuming that the bounds of the item to be manufactured are within the manufacturing limits of the machine. For tests including disks discussed above, typical sizes obtained were of a 5 mm diameter and 1 mm height, and beads discussed above were of 6 mm diameter with internal holes of 3 mm sizes, however this is by no means representative of the full capability of the manufacturing capability of the devices used. For other common biomedical applications, common configurations of devices to be manufacture include, but are not limited to, screws, nails, device covers, catheters, IV line ports, and any other medical device that can be fabricated. Additionally filaments themselves could just be implanted as necessary or made into small "splinters" to be inserted in a manner to brachytherapy seeds with no need for removal in the case of bio-absorbable materials.

One of several benefits that 3D fabrication has over older fabrication methods involve the customization made possible by 3D fabrication. The layered filament can be put down in a determined layer height. Cheaper consumer 3D printers allow for 50 um to 400 um layer size. Commercial versions have much finer resolutions. This allows for more precise manufacturing and also increase the surface area from standard injection molding. The percent fill of a manufactured device can also be modified. A construct that is only for example 20% filled with plastic will have the interior made into a "honey comb" support structure. This allows for more surface area for elution. This also allows for a lower weight of the construct. Less and hollow material can be absorbed by the body quicker. Less material can be used which can lower the cost of manufacturing in the case of expensive additives or biomaterials. The honey comb structure void content (i.e., volume of empty space to volume of solid material) can be, in alternative embodiments, at least 5%, 10%, 20%, 30%, 40%, 50%, 60%, 70%, 80%, 90%, or 95%.

Bioactive agents can also include almost any powdered material or metal. It is possible to make filaments including such diverse compounds but not limited to iron, barium, gadolinium, tin, bismuth, copper or sodium iodide. This allows for the usage of almost any element on the periodic table or molecule if ground to a proper size that it will not clog extruder or 3D printer head nozzles. Melting points of additives are important to note in the filament manufacturing process to keep a uniform diameter. Many Tin/Bismuth alloys will melt at similar ranges to PLA and ABS plastics. The usage of any material leads to possibilities in custom printed radiation shielding.

In another example (example 15), filaments were created using an extrusionbot filament extruder of 1%-25% Iron, 1%-25% gadolinium, 1-20% Sodium Iodide and 1%-15% Tin/Bismuth alloy for 3D fabrication using an oil coating and layer-by-layer coating method. Some filaments that were not uniform were cut up and re-extruded. It is necessary at times of non-uniform filament to cut it up into pellets or granules or grind into powders and re-extrude. A 25% iron-PLA filament was cut up and re-extruded. The filament was then printed into 1 inch by 1 inch squares of a 1 mm height with 100% fill as testing squares for radiation shielding.

As noted in this description almost any biological compound or molecule that does not degrade at extrusion and print temperatures can be added to filament to develop a construct. Progesterone, Estrogen and Testosterone as well as many other hormones have sufficiently high degradation temperatures that they can be mixed into filaments when using plastics with lower melting points including but not limited to PCL. Any construct could be printed and made to elute this hormones. This could allow for custom fabrication of intrauterine devices for birth control as a form of personalized medicine. Customized sizes and elutions rates could created based on the medical condition or usage. Many current commercial IUDs are made with copper. Copper powder or ions can be built into the filament or a final construct that could release them in addition to hormones. Spermicidal compounds with proper degradation points could also be used. IUDs made of bio-absorbable materials may not need to be removed or could cause less complications if left in place for years. Adding very insoluble antibiotics such as nitrofurantoin to the plastic could add long-term antimicrobial properties. Additionally, the extruded filaments themselves could be slightly heated and hand molded into a desirable shape. For example E1, E2, E3 and progesterone where mixed with PCL polymers and extruded and printed into IUDs, meshes and beads or onto pessary devices.

Medical devices require sterilization. Heating for extrusion and printing may not be enough for all usages. Pellets and powders may need to be sterilized by heat/autoclave, alcohol, UV light, radiation or an appropriate medical sterilization process. Additives (Bioactive powder, HNTs etc. . . . ) or even coating oils may also need to be sterilized by these processes. The entire item of equipment may be sterilized or alternatively, only the internal parts that will touch any portion of the medical print may need to be sterilized to appropriate standards. There are many guidelines such as the CDC's 2008 Guideline for Disinfection and Sterilization in Healthcare Facilities, 2008 by William Rutala.

One difficulty in custom manufacturing of a specialized filament lies in the limitations of extrusion devices. Filament extrusion devices are not made with the intention of quickly changing the pipe or auger after a few or every extrusion. Purging a plastic extrusion device can take substantial amounts of time and there is no easy way to ensure that all additives have been completely removed. One embodiment of a solution is to develop a device with a quick release auger and pipe. If the hopper and feed system connecting to the auger/pipe opening is also interchangeable then a completely or partially new and sterilized internal pathway for the filament can be created every time a new batch is made. The nozzle assembly or "extuder die" can also be cheaply replaced or autoclaved.

Figure 9:
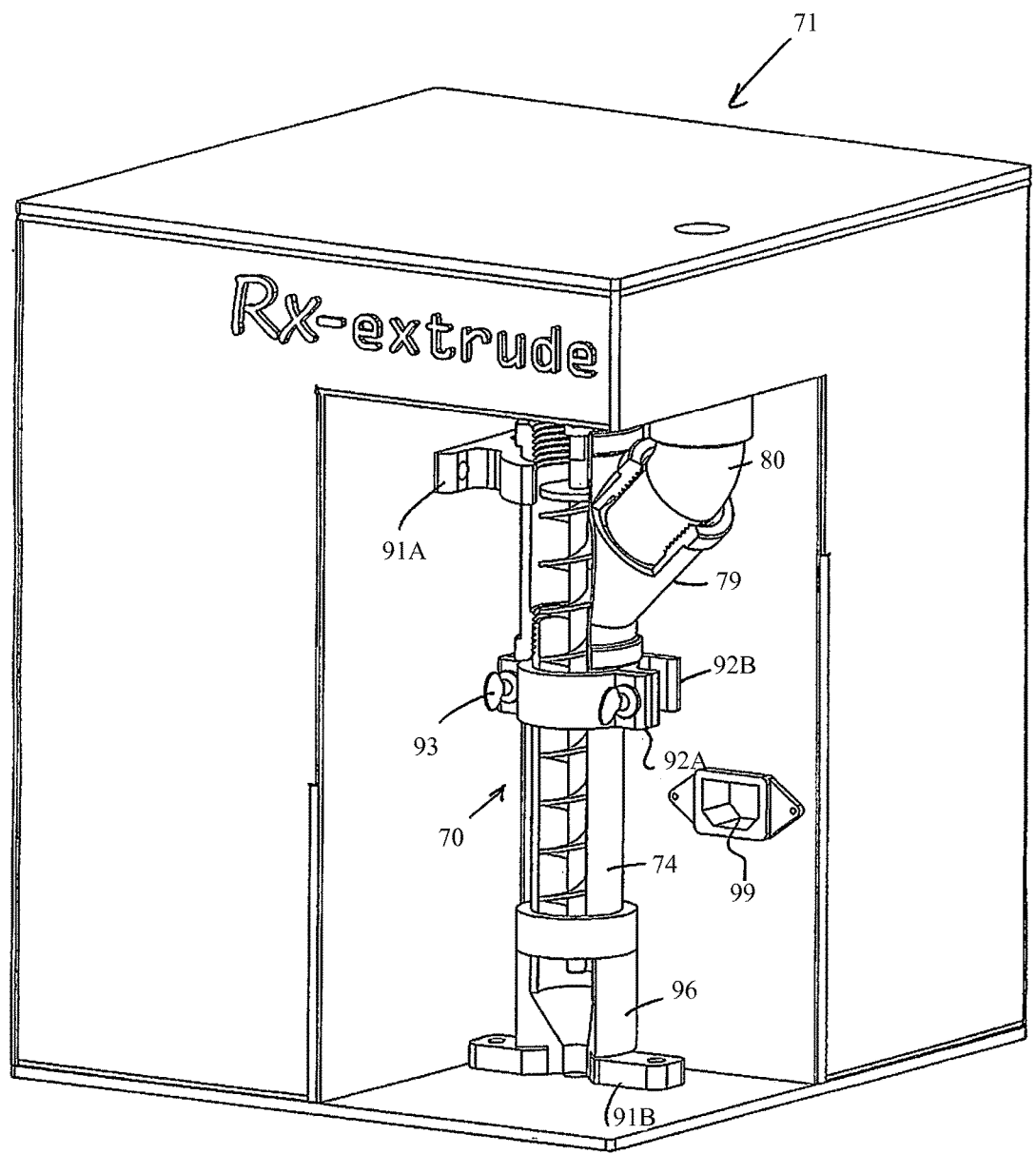
FIG. 9 illustrates an auger type extruder device.
Figure 10:
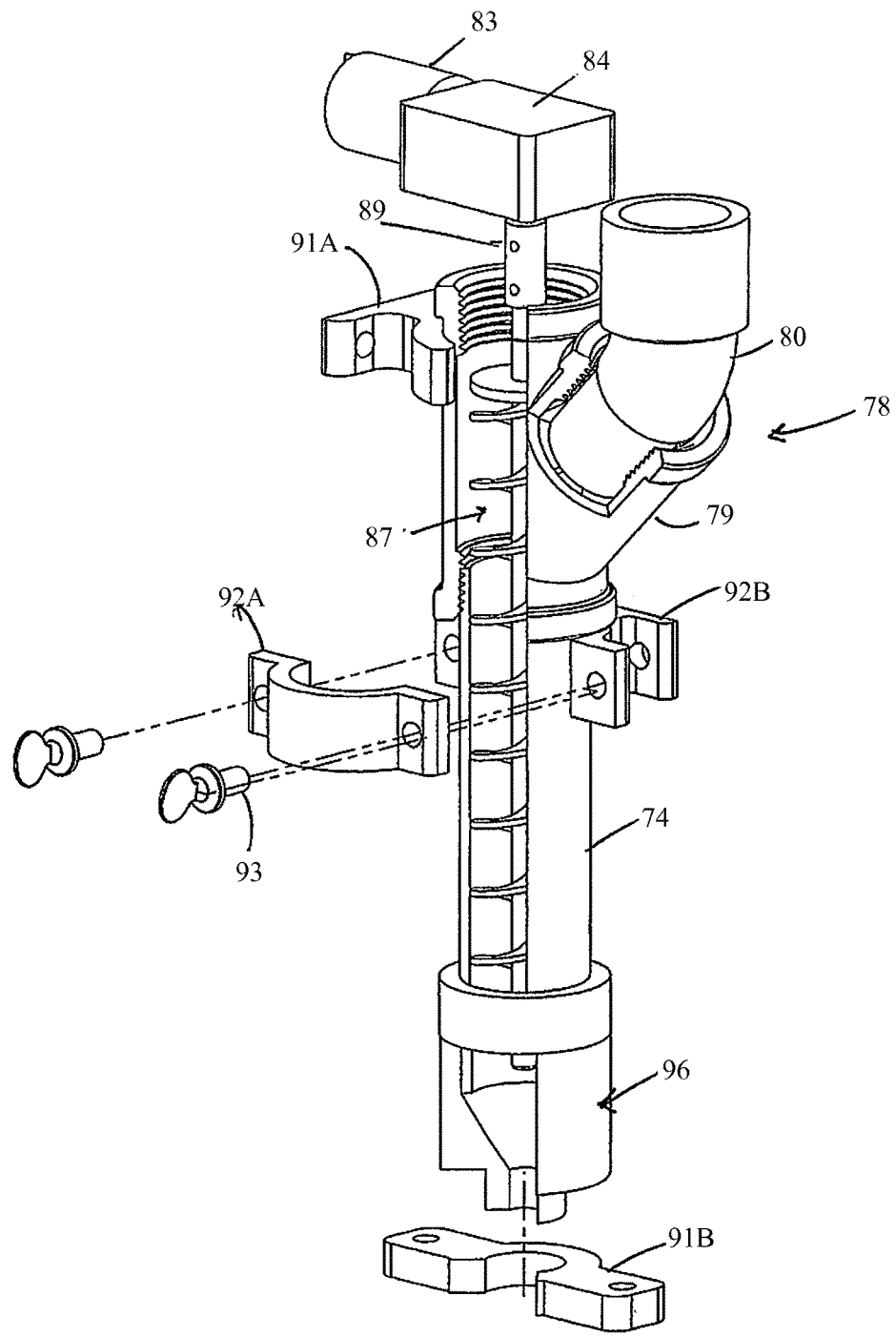
FIG. 10 illustrates a sectional perspective view of the FIG. 9 extruder device.
Figure 11:
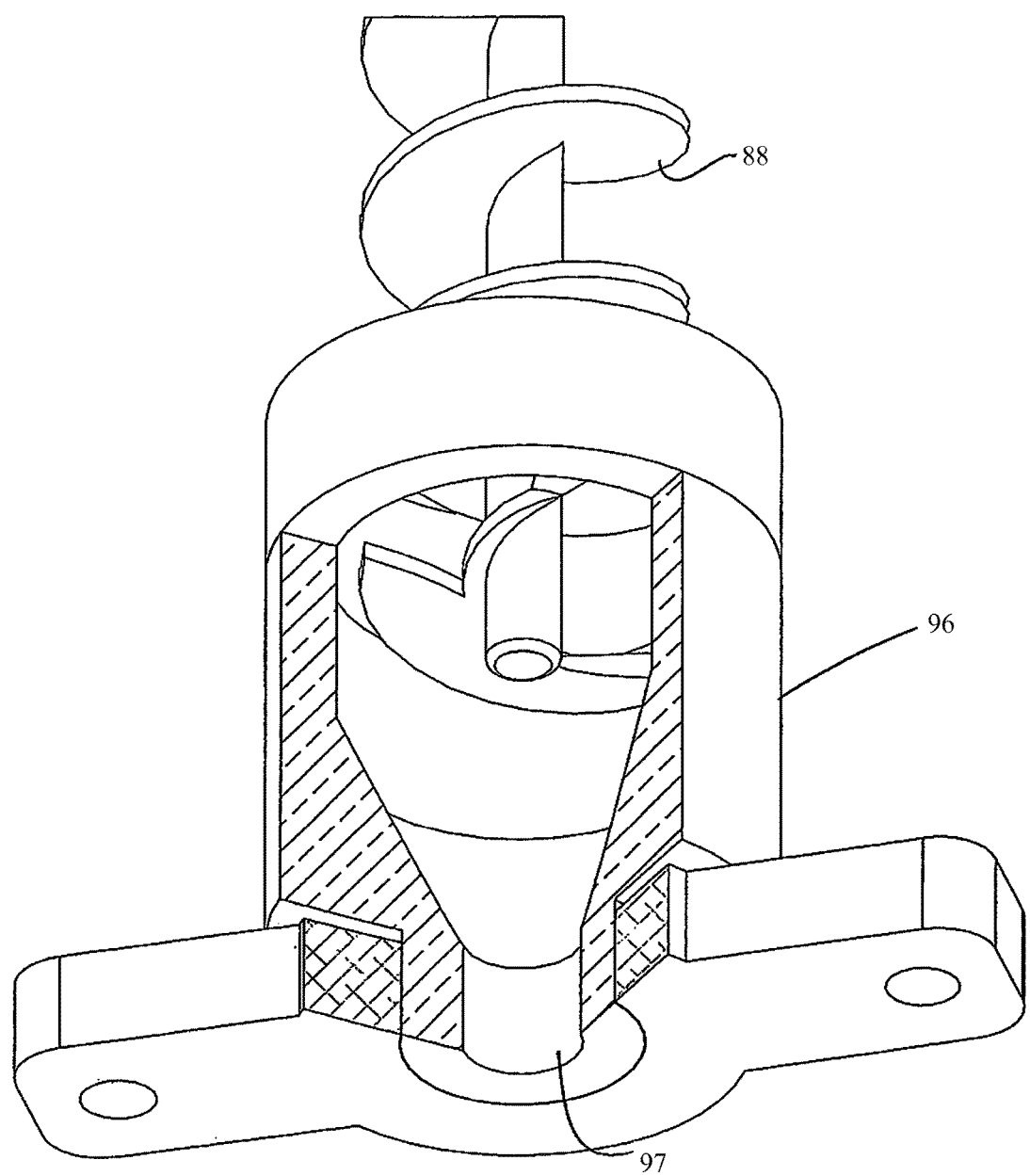
FIG. 11 illustrates the nozzle assembly of the FIG. 9 extruder device.

FIGS. 9 to 11 illustrate one embodiment of an extruder device 70 utilizing an auger component. FIG. 10 shows the main components of the extruder device 70 including barrel 74, feed inlet 78, motor 83, gearbox 84, auger 87, and nozzle assembly 96. The feed inlet 78 will include a feed tube 79 and feed insert 80 which slides into feed tube 79. It may be readily visualized how rotational speed from motor 83 is reduced and torque increased by gearbox 84 and the torque transferred to auger 87 via the connecting collar 89 which joins the gearbox's output shaft with the central shaft of auger 87. The extrudable material (e.g., a polymer/bioactive agent as described herein) is introduced into the barrel 74 through the feed inlet 78 near the top of auger 87. As suggested in FIG. 11, the auger blades 88 will force the extrudable material downward into the nozzle assembly 96. Although hidden from view in FIG. 11, the nozzle assembly 96 will include a heating element which heats the assembly and bring the extrudable material to its meltflow temperature prior to the extrudable material exiting nozzle aperture 97.

Returning to FIG. 9, it is seen that a series of brackets 91 and 92 engage extruder device 70 and maintain its position in cabinet 71. Upper open-face bracket 91A engages the upper portion of barrel 74 and lower open-face bracket 91B engages the end of nozzle assembly 96. The open-face brackets 91A and 91B will be fixed the wall and floor of cabinet 71 respectively. A third closed bracket 92 consists of two components, wall component 92B fixed to the cabinet wall and removable component 92A. The thumb screws 93 are employed to tighten bracket component 92A to 92B together and thus fix extruder device 70 in place within cabinet 75. Although not shown for the sake of clarity, it will be understood that a power cord would engage socket 99 and extend to the heating element in nozzle assembly 96. The brackets will allow for extruder device 70 to be rapidly removed from cabinet 75 by the disconnecting of bracket component 92A from component 92B, feed insert 80 from feed tube 79, and connecting collar 89 from the auger shaft. This easy and rapid removal of the extruder device 70 is advantageous for avoiding cross-contamination in that a new extruder device can easily be employed when extruding a different material (typically having a different bioactive compound).

The standard die has a hole drilled into it the same diameter as the desired filament. Metals, ceramics or other thermally appropriate materials may be used for this portion of the extruder. Some materials may expand or contract after extrusion resulting in a need for a die larger or smaller than the filament desired. Using a cooling fan, temperature and humidity controlled room or a water bath may be necessary to rapidly solidify certain extruded materials. Additionally, a die can have an elongated guide tip (as in the FIG. 5 embodiment) of the desired diameter or "straw" of desired length going off of it to provide additional controlled cooling of the material after exiting the extrusion chamber. This "straw" could be an alternative material such as a thermally shielded ceramic. The straw portion can also be created in a manner that allows it to be screwed on and easily removable.

One skilled in the art would note that adaptation of this technology to fabrications methods beyond fused deposition modeling can be possible. Selective laser and heat sintering processes can be used provided there is not excess degradation of the additives. Additionally, light polymerization techniques that harden a liquid can be used if additives can be uniformly or regularly mixed into the liquid polymers. For example a silver particle can be placed into the liquid polymer and tympanostoym tubes can be fabricated that are bioactive.

It should be noted that localized elution via the constructs can be highly favorably in terms of targeted drug delivery, controlled release of drug delivery and protection from nephrotoxicity or other toxicities associated with excess systemic drug release.

One concern in the creation of bioactive constructs involve the temperatures that result in thermal degradation. While certain antibiotics such as aminoglycosides have high thermal stability others do not. One option is to use a method to spray an additive on the constructs or layer of filament becoming the construct after it leaves the 3D printer head. Many polymers in the case of FDM cool very quickly to below the thermal degradation point of an additive of interest. The additive can be sprayed or layered down in an appropriate amount as needed with a separate nozzle or printer head. Many cooling polymers maintain a tacky nature that allows them to hold an additive and release them as they degrade. Multiple print heads of different varieties may be needed to lay down a plurality of materials and or additives. Multiple additive manufacturing techniques can have these concepts applied. For example, laser sintering could still have additives sprayed onto each layer as the sintering process is occurring.

Figure 12:
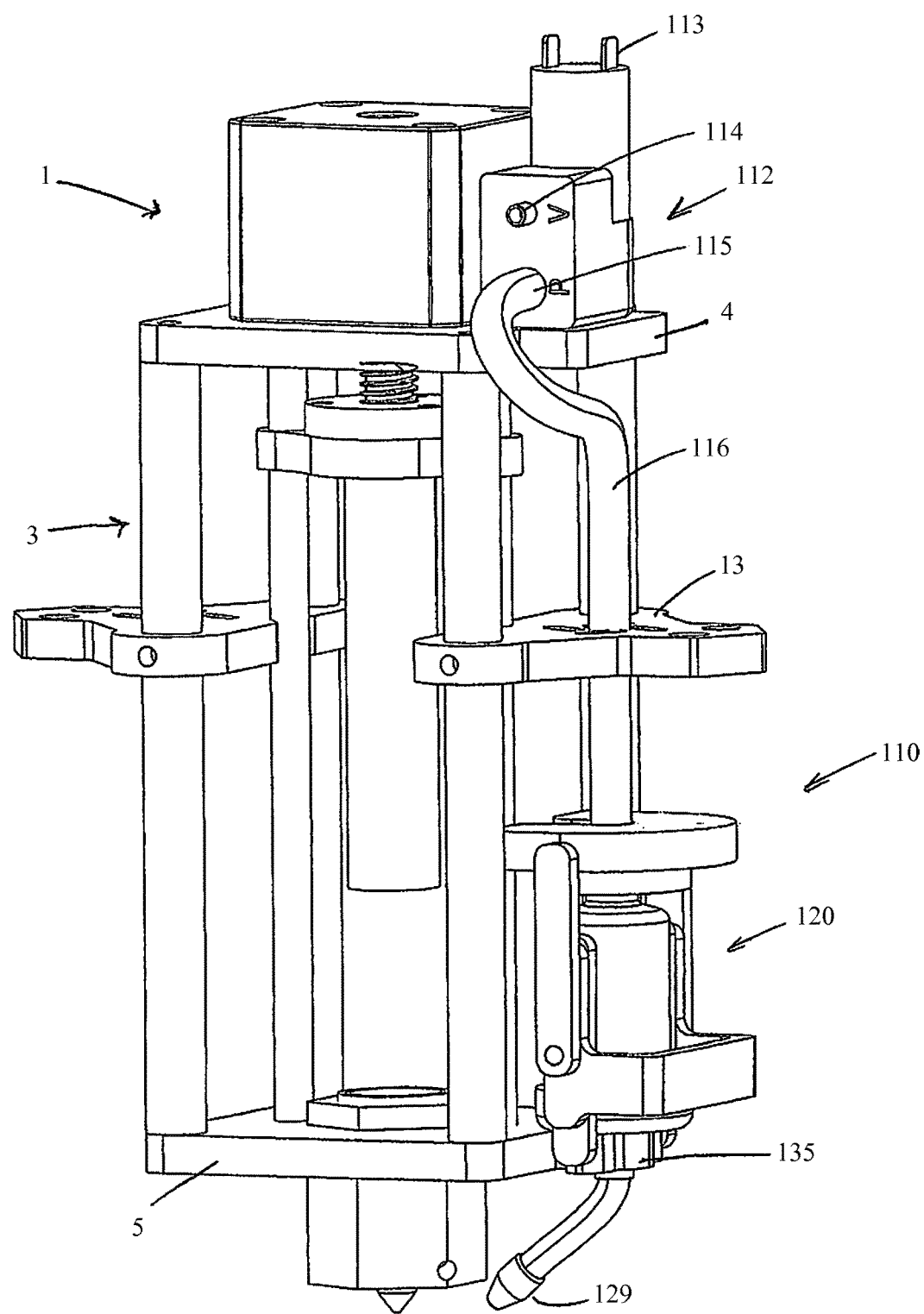
FIG. 12 illustrates a perspective view of a printer cartridge including a bioactive agent spray assembly.

FIGS. 12 to 17 illustrate a modified version of the 3D printer cartridge seen in FIG. 3A which incorporates one embodiment of this spraying concept. FIG. 12 shows the 3D printer cartridge 1 as further including a sprayer assembly 110 mounted on frame 3. Sprayer assembly 110 generally comprises a pump mechanism 112, a vial latch assembly 120, and a sprayer nozzle 129. In the illustrated embodiment, pump mechanism 112 is mounted on frame upper plate 4 and is an electrically driven diaphragm pump having vacuum port (air inlet) 114, pressure port (air outlet) 115, and electrical contacts 113. Although the pump capacity could vary depending on the embodiment, the pump shown has a 1.8 liter/min capacity and should be suitable for many applications. Although this embodiment of the pump mechanism is a diaphragm pump, the term "pump mechanism" encompasses any manner of creating pressure or force which will drive the bioactive agent through the sprayer nozzle. For example, a pump mechanism could include a syringe pump, a piston (like plunger 15 described in reference to FIG. 3A), any other conventional or future developed mechanism for generating pressure or force.

Figure 13:
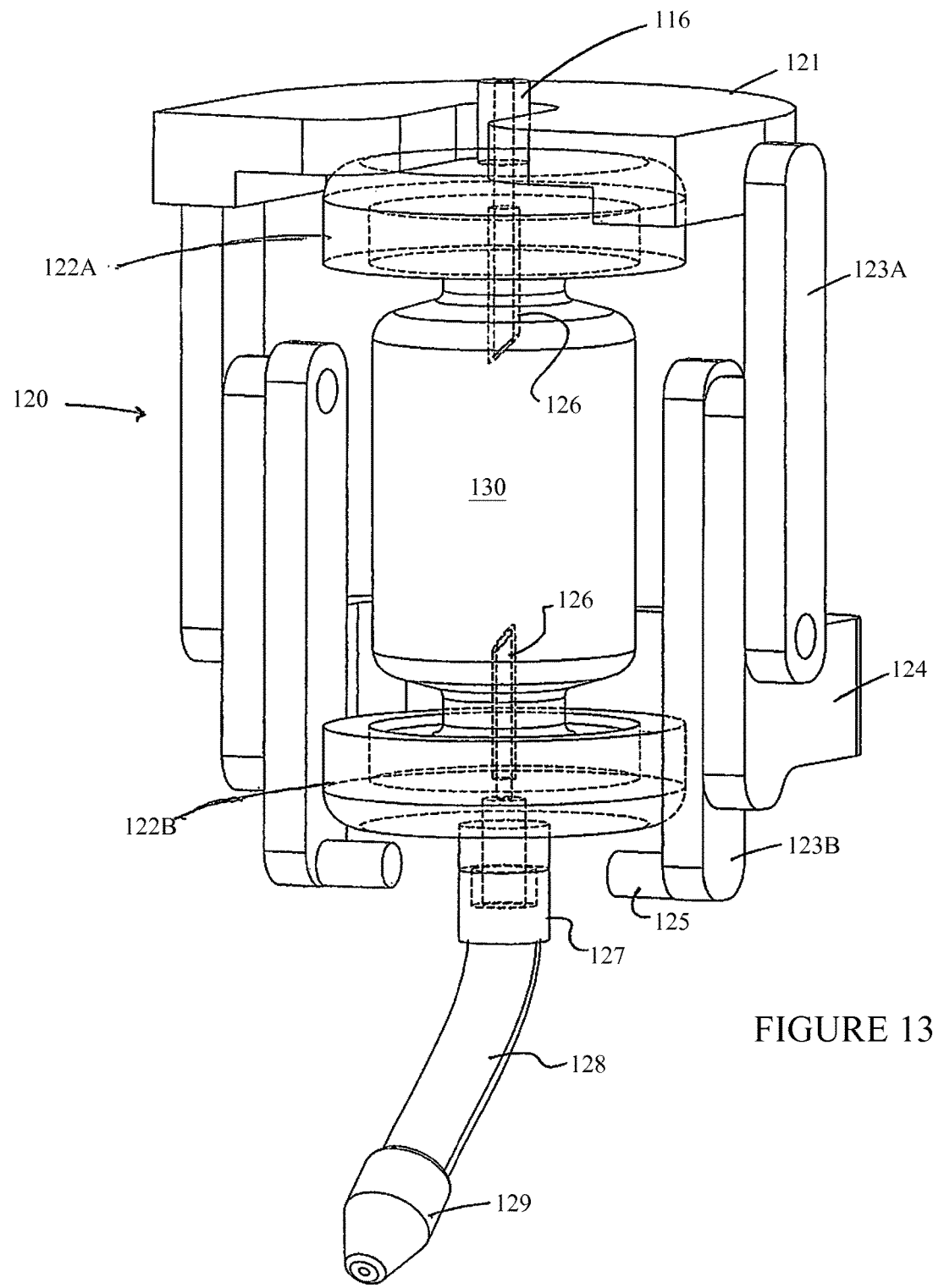
FIG. 13 illustrates one example of a vial latch assembly utilized with the FIG. 12 printer cartridge embodiment.
Figure 14:
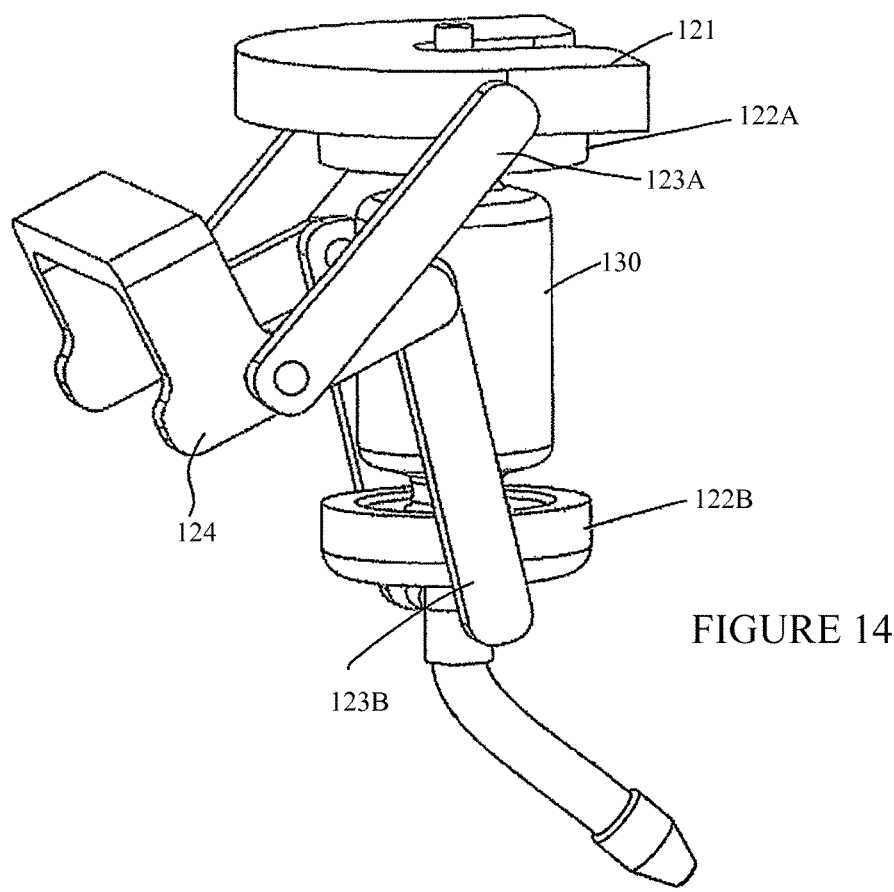
FIG. 14 illustrates another view of the latch mechanism of the FIG. 13 embodiment.
Figure 15:
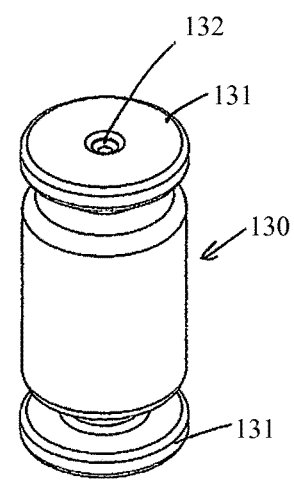
FIG. 15 illustrates one example of a double-ended vial.
Figure 16:
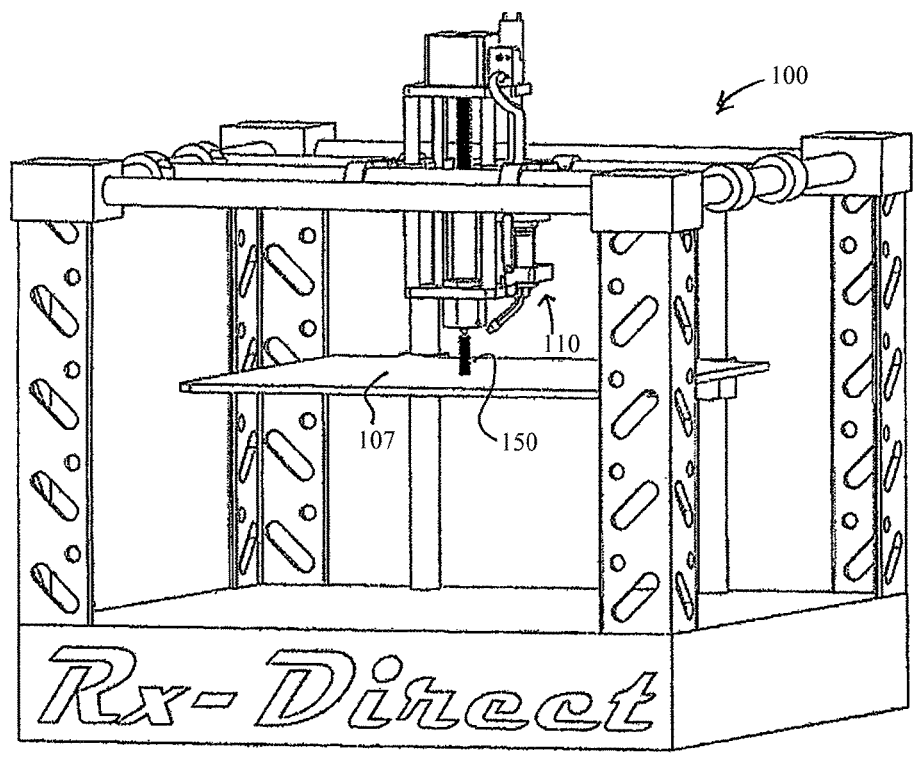
FIG. 16 illustrates a 3D printer with a spaying assembly operating upon an implant device.
Figure 17:
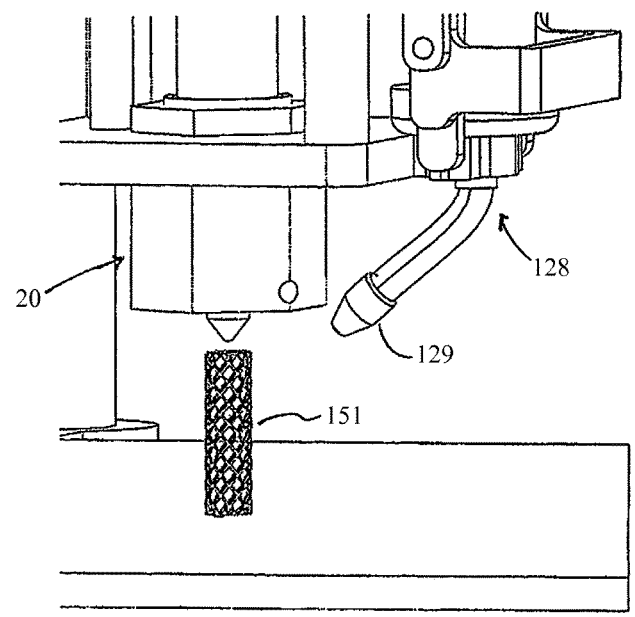
FIG. 17 illustrates an enlarge view of the FIG. 16 spaying assembly and implant device.

A hose 116 will extend from air outlet 115, through attachment plate 13, and to the vial latch assembly 120, which is more clearly shown in FIGS. 13 and 14. FIG. 13 suggests how the vial latch assembly includes the latch top 121, upper and lower vial caps 122A and 122B, upper and lower extension arms 123A and 123B, and the locking cradle 124. Although not part of the vial latch assembly itself, FIG. 13 illustrates a vial 130 (which would contain a bioactive agent) positioned in the latch assembly. FIG. 15 suggests how in this embodiment, vial 130 is a conventional double-ended vial having two head sections 131 and a self-sealing diaphragm 132 in each head section. Returning to FIG. 13, each vial cap has a needle 126 formed thereon which will be capable of extending through the vial's self-sealing diaphragm 132. The needle 126 in upper vial cap 122A attaches to hose 116 while the needle 126 in lower vial cap 122B is attached to connecting collar 127, which provides the connection to sprayer nozzle 129 via hose 128. Typically hose 128 will be sufficiently rigid to reliably maintain the position of sprayer nozzle 128 relative to extruder nozzle assembly 20.

FIG. 14 suggests how vial latch assembly forms a type of folding latch assembly with linkages which operate to allow the vial caps to transition between an open position where vial 130 may be installed/removed and a closed position where vial 130 is held securely in place. When locking cradle 124 is pulled upward and away from the vial caps, extension arms 123 unfold and allow vial caps 122 to separate sufficiently far for needles 126 to be withdrawn from vial 130. On the other hand, when locking cradle 124 is moved adjacent to lower vial cap 122B, extension arms 123 fold and draw vial caps 122 closer together as seen in FIGS. 12 and 13. The vial latch assembly 120 could be secured to the frame 3 in any number of ways. The FIG. 12 embodiment shows the latch top 121 connected to the frame spacer columns and the pins 125 (see FIG. 13) on lower extension arms 123B engaging the bottom connector 135 (see FIG. 12), which is in turn connected to lower frame plate 5.

FIGS. 16 and 17 illustrate the printer cartridge of FIG. 12 installed in the 3D printer 100. FIG. 16 shows an implant 150 on elevating floor 107 beneath the extruder nozzle and the sprayer nozzle. As better seen in FIG. 17, the implant 151 (a stent in FIG. 17) can be subject to a spray of bioactive agent from nozzle 129 since spraying nozzle 129 is positioned adjacent to the tip of extruder nozzle assembly 20. The exact sequence of extruder nozzle assembly 20 depositing the stock material and sprayer nozzle 129 apply the bioactive agent can vary greatly from embodiment to embodiment. In one example, the bioactive agent is sprayed onto the implant substantially continuous during a time when the implant is being formed by the printer, thereby uniformly covering the implant. In another embodiment, the bioactive agent is sprayed onto only select portions of the implant, leaving other portions uncoated with the bioactive agent. In a still further embodiment, cooling intervals are provided between the extruding of a quantity of melted stock material and the spraying of the bioactive agent onto that quantity of stock material, thereby insuring the stock material has cooled sufficiently not to denature or degrade the bioactive agent applied to the implant. Although the Figures only show one sprayer assembly, other embodiments could have multiple sprayer assemblies, either on the same printer cartridge or on different printer cartridges.

In other embodiments, microspheres or small amounts of additive can be added in clusters to specific areas of a construct. This could lead to additional burst releases as a construct degrades within the body. A special print head or mechanism to lay down small microspheres or grains of material can be used.

It may also be possible to use ultrasound, laser or a similar energy producing device to induce fractures in a construct to increase the pace of bioactive drug release.

One embodiment of a construct may be a bead or seed to mark the location of construct. The seed could be 3D printed. This could be a traditional solid construct. 3D printing also has the advantage of a hollow or honey combed fabrication based on percent fill. Laser sintering could be used to create a marker that will have hollow areas that do not block radiation dosage to a tumor. A custom shaped marker could also be created. Additionally doped filaments with radio-opaque materials could be used as a solid or honey-comb print as a marker. Certain doped filaments that are biodegradable could be used. This could result in adsorption of the edges by the body during the weeks of treatment to decrease the size of the marker and allow less interference with targeting of the tumor.

One embodiment of construct may be surgical mesh that is customized. The mesh could be a specific size, have fasteners, biological additives or other additives singularly of in combination. A biodegradable mesh could avoid the need for removal. A mesh with a contrast agent like iron or barium could be easier to visualize on X-ray. An existing surgical mesh could be coated with a plurality of layers to give unique capabilities. Layers could include permanent or adsorbable materials. Layers could be bioactive. Layers could be rigid or flexible.

One concept would be to use the arms of a surgical robot that have been fitted with small printing devices to print the mesh in place. FDM is just one of a variety of options for printing.

Spray coating a mesh or spider web could be done using an airbrush type robotic aperture. The airbrush could be used in either minimally invasive or open surgery. It could be used by robotic or manual control. There are many methods known to those skilled in the art to use an airbrush or atomizer to spray a mesh material. These materials can be adsorbable polymers/compounds or those that will not break down within the body.

The printing heads discussed for bioactive 3D printing could be fitted onto existing laproscopic surgery tools or robotic laproscopic surgery tools for use. This could allow for minimally invasive fabrication directly within the patient's body.

One embodiment for 3D printing are custom surgical ports that could be bioactive. A concern in surgical oncology is seeding. A methotrexate or chemotherapeutic eluting port would alleviate these concerns.

An alternative to 3D printing them is to use a spray coating apparatus to put a film onto the already manufactured port. This could be done in the operating room in advance of a surgery. Custom biological spray coatings could be done to prevent seeding that are personalized to the individual cancer.

It should be noted that almost all methods of additive manufacturing that include but are not limited to fused deposition modeling and laser sintering (both powder and liquid polymer) can be used in construction of the following non-limiting examples.

The embodiments described herein can use singularly or in combinations of materials that have radioactive components, chemotherapeutic components, radio-sensitizer components or shielding components. Many techniques in radiation oncology are minimally invasive. The techniques for construct creation or placement may be done with a surgical robot or surgical port. It is important to note that combinations of the methods and examples listed above may be advantageous.

Nonlimiting examples of implants which may be created or enhanced with the above described methods and apparatuses include catheters, beads, stents, bone grafts, IUDs, pessaries, meshes, sutures, dressings, screws, rods, pins, and plates.

Additive manufacturing onto existing medical items can be done. For example estrogen eluting PCL material was fabricated onto an existing pessary model device for direct application and treatment of muscle prolapse.

Bioactive printed constructs could have applications in industries outside of the medical or biotechnology uses. These devices can fill industrial needs for specifically sized and bioactive eluting constructs or devices and materials designed for corrosion-resistance, anti-fouling, or toxic waste removal or remediation and air or water treatment.

Other aspects and advantages will become apparent upon consideration of the following detailed description and the attached drawings, in which like elements are assigned like reference numerals. Numerous modifications will be apparent to those skilled in the art in view of the foregoing description. Accordingly, this description is to be construed as illustrative only and is presented for the purpose of enabling those skilled in the art to make and use what is herein disclosed and to teach the best mode of carrying out same. The exclusive rights to all modifications which come within the scope of this disclosure are reserved.

The invention claimed is:

1. A method for manufacturing a bioactive implant comprising the steps of:
   a. forming a mixture of at least one of an antimicrobial, an antiseptic, or a chemo-therapeutic with a polymer stock material, wherein (i) the antimicrobial, antiseptic, or chemo-therapeutic ranges from about 0.01% to about 75% by weight of the mixture, and (ii) the mixture further comprises an adhering agent enhancing the adhesion of the bioactive agent to the polymer stock material, the adhering agent being at least one from the group consisting of biological oils, silicone-based substances, and water;
   b. heating the mixture to an approximate meltflow temperature of the polymer stock material; and
   c. forming the mixture into a shape of a stent or a catheter using 3D printing.

2. The method of claim 1, wherein the meltflow temperature does not substantially exceed a degradation temperature of the bioactive agent.

3. The method of claim 2, wherein the meltflow temperature is less than about 220° C.

4. The method of claim 1, wherein the polymer stock material is at least one from the group consisting of poly(methyl methacrylates), acrylonitrile butadiene styrene(s), polycarbonate(s), polylactides, polyglycolides, polycaprolactones, polyanhydrides, polyorthocarbonates, polyvinylpyrrolidone chitosan, and a linear polysaccharide.

5. The method of claim 1, further comprising a second bioactive agent which is at least one from the group consisting of metals, proteins, peptides, polypeptides, sugars, carbohydrates, lipids, hormones, minerals, vitamins, and radioactive materials.

6. The method of claim 1, further comprising the step of providing an implant and transitioning the mixture into the shape of the implant by coating the implant with the mixture.

7. A method for manufacturing a bioactive implant comprising the steps of:
   a. forming a mixture of at least one of an antimicrobial, an antiseptic, or a chemo-therapeutic with a polymer stock material, wherein (i) the antimicrobial, antiseptic, or chemo-therapeutic ranges from about 0.01% to about 75% by weight of the mixture, and (ii) the mixture further includes nanostructures from the group consisting of carbone, grapheme, halloysite, titanium, zinc nanotubes and oxidized forms thereof;
   b. heating the mixture to an approximate meltflow temperature of the polymer stock material; and
   c. forming the mixture into a shape of a stent or a catheter using 3D printing.

8. A method for manufacturing a bioactive implant comprising the steps of:
   a. forming a mixture of at least one of an antimicrobial, an antiseptic, or a chemo-therapeutic with a polymer stock material;
   b. heating the mixture to an approximate meltflow temperature of the polymer stock material;
   c. forming the mixture into a shape of a stent or a catheter using 3D printing; and
   d. wherein the mixture further includes at least one mineral from the group consisting of magnesium dioxide, zinc oxide, titanium dioxide, and clay nanoparticles.

9. The method of claim 1, wherein the antimicrobial is at least one from the group consisting of aminoglycoside, cephalosporin, macrolide, lincosamide, penicillin, Quinolone, Rifamycins, Sulfa, tetracycline, cabapenems, polypeptides and colloidal silver.

10. A method for manufacturing a bioactive implant comprising the steps of:
    a. forming a mixture of at least one of an antimicrobial, an antiseptic, or a chemo-therapeutic with a polymer stock material, wherein the antimicrobial, antiseptic, or chemo-therapeutic ranges from about 0.01% to about 75% by weight of the mixture;
    b. heating the mixture to an approximate meltflow temperature of the polymer stock material; and
    c. forming the mixture into a shape of a stent or a catheter using 3D printing, wherein the printing step includes printing a honeycombed structure having a void content of at least 5%.

11. The method of claim 1, wherein the polymer stock material's temperature is reduced below the material's ductile-brittle transition temperature before the material is reduced to smaller sized components.

12. The method of claim 10, wherein the meltflow temperature does not substantially exceed a degradation temperature of the bioactive agent.

13. The method of claim 12, wherein the meltflow temperature is less than about 220° C.

14. The method of claim 10, wherein the polymer stock material is at least one from the group consisting of poly(methyl methacrylates), acrylonitrile butadiene styrene(s), polycarbonate(s), polylactides, polyglycolides, polycaprolactones, polyanhydrides, polyorthocarbonates, polyvinylpyrrolidone chitosan, and a linear polysaccharide.

15. The method of claim 10, further comprising a second bioactive agent which is at least one from the group consisting of metals, proteins, peptides, polypeptides, sugars, carbohydrates, lipids, hormones, minerals, vitamins, and radioactive materials.

16. The method of claim 7, wherein the meltflow temperature does not substantially exceed a degradation temperature of the bioactive agent.

17. The method of claim 16, wherein the meltflow temperature is less than about 220° C.

18. The method of claim 7, wherein the polymer stock material is at least one from the group consisting of poly (methyl methacrylates), acrylonitrile butadiene styrene(s), polycarbonate(s), polylactides, polyglycolides, polycaprolactones, polyanhydrides, polyorthocarbonates, polyvinylpyrrolidone chitosan, and a linear polysaccharide.

19. The method of claim 7, further comprising a second bioactive agent which is at least one from the group consisting of metals, proteins, peptides, polypeptides, sugars, carbohydrates, lipids, hormones, minerals, vitamins, and radioactive materials.

* * * * *